(12) United States Patent
Cockerill et al.

(10) Patent No.: US 10,603,319 B2
(45) Date of Patent: Mar. 31, 2020

(54) PYRIMIDINE DERIVATIVES AND THEIR USE IN TREATING OR PREVENTING A RESPIRATORY SYNCYTIAL VIRUS INFECTION

(71) Applicant: REVIRAL LIMITED, Stevenage (GB)

(72) Inventors: Stuart Cockerill, Stevenage (GB); Matthew Barrett, Stevenage (GB)

(73) Assignee: REVIRAL LIMITED, Stevenage (GB)

( * ) Notice: Subject to any disclaimer, the term of this patent is extended or adjusted under 35 U.S.C. 154(b) by 0 days.

(21) Appl. No.: 16/322,264

(22) PCT Filed: Aug. 3, 2017

(86) PCT No.: PCT/GB2017/052257
§ 371 (c)(1),
(2) Date: Jan. 31, 2019

(87) PCT Pub. No.: WO2018/025043
PCT Pub. Date: Feb. 8, 2018

(65) Prior Publication Data
US 2019/0167683 A1      Jun. 6, 2019

(30) Foreign Application Priority Data
Aug. 4, 2016 (GB) .................................. 1613475.1

(51) Int. Cl.
| | | |
|---|---|---|
| C07D 403/06 | (2006.01) |
| A61K 31/506 | (2006.01) |
| A61P 31/14 | (2006.01) |
| A61K 9/20 | (2006.01) |
| A61K 45/06 | (2006.01) |
| A61K 31/5377 | (2006.01) |
| A61K 31/541 | (2006.01) |
| C07D 403/14 | (2006.01) |
| C07D 401/14 | (2006.01) |
| C07D 405/14 | (2006.01) |
| A61K 9/00 | (2006.01) |

(52) U.S. Cl.
CPC .......... *A61K 31/506* (2013.01); *A61K 9/0019* (2013.01); *A61K 9/2009* (2013.01);
(Continued)

(58) Field of Classification Search
CPC .. C07D 403/06; C07D 403/14; C07D 405/14; A61K 31/506; A61K 31/5377; A61K 31/541
(Continued)

(56) References Cited

U.S. PATENT DOCUMENTS

| 5,256,668 A | 10/1993 | Hsu et al. |
| 2016/0318943 A1* | 11/2016 | He ..................... C07D 403/06 |

FOREIGN PATENT DOCUMENTS

| WO | 02/072290 A1 | 9/2002 |
| WO | 03/053344 A2 | 7/2003 |
| WO | 2010/103306 A1 | 9/2010 |
| WO | 2013/068769 A1 | 5/2013 |
| WO | 2014/060411 A1 | 4/2014 |
| WO | 2014/184163 A1 | 11/2014 |
| WO | WO 2015/085844 | * 6/2015 |
| WO | 2016/001077 A1 | 1/2016 |
| WO | 2016/055780 A1 | 4/2016 |
| WO | 2015/085833 A1 | 6/2016 |

OTHER PUBLICATIONS

K.D. Combrink et al., Biorganic & Medicinal Chemistry Letters, 17 (2007), 4784-4790.
(Continued)

*Primary Examiner* — Deepak R Rao
(74) *Attorney, Agent, or Firm* — Quarles & Brady LLP

(57) ABSTRACT

Pyrimidine derivatives of formula (I) wherein: Z is a direct bond or —$(CH_2)_n$— wherein n is 1 or 2; one of X and Y is N, CH or CF, and the other of X and Y is CH; one of $R^1$ and $R^2$ is selected from —NHR, —$NR_2$, —OR, —SR, —S(O)R, —$S(O)_2$R and a group of the following formula (A) and the other of $R^1$ and $R^2$ is selected from —NHR', —OH, —OR' and a group of the above formula (A); R is unsubstituted $C_1$-$C_6$ alkyl; R' is a group selected from $C_1$-$C_6$ alkyl, 5- to 12-membered aryl and $C_3$-$C_6$ cycloalkyl, which group is unsubstituted or substituted; W is —$(CH_2)_m$—, —$CH_2$—O—$CH_2$—, —$CH_2$—S—$CH_2$— or —$CH_2$—$S(O)_2$—$CH_2$—; p is 1, q is an integer of 1-6 and V is N; or p is 1, q is 0 and V is CH; or p is 0, q is 0 and V is N; r is 0 or 1; and $R^3$ is —$(CH_2)_s$—$NH_2$ or —$(CH_2)_s$—OH wherein s is 0 or an integer of 1 to 4; and the pharmaceutically acceptable salts thereof are inhibitors of RSV and can therefore be used to treat or prevent an RSV infection.

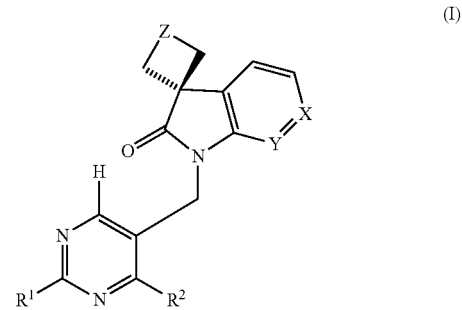

(I)

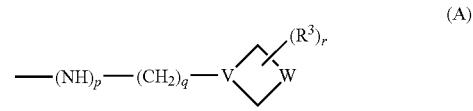

(A)

14 Claims, No Drawings

(52) U.S. Cl.
CPC .......... *A61K 9/2013* (2013.01); *A61K 9/2018* (2013.01); *A61K 9/2059* (2013.01); *A61K 31/5377* (2013.01); *A61K 31/541* (2013.01); *A61K 45/06* (2013.01); *A61P 31/14* (2018.01); *C07D 401/14* (2013.01); *C07D 403/06* (2013.01); *C07D 403/14* (2013.01); *C07D 405/14* (2013.01)

(58) Field of Classification Search
USPC ...... 544/122, 322, 323, 324; 514/235.8, 275
See application file for complete search history.

(56) References Cited

OTHER PUBLICATIONS

Meanwell et al., Drugs of the Future, 32 (2007) 441-455.
J. Med. CHem., 2019, 62(7), pp. 3206-3227 (Cockerill et al.).
International Preliminary Report on Patentability, together with Written Opinion and International Search Report, dated Feb. 5, 2019 in connection with PCT/GB2017/052257 International Search Report.

\* cited by examiner

PYRIMIDINE DERIVATIVES AND THEIR USE IN TREATING OR PREVENTING A RESPIRATORY SYNCYTIAL VIRUS INFECTION

CROSS-REFERENCE TO RELATED APPLICATIONS

This application represents the national stage entry of PCT International Application No. PCT/GB2017/052257 filed Aug. 3, 2017, which claims priority to Great Britain Patent Application 1613475.1 filed Aug. 4, 2016, the contents of which are hereby incorporated herein by reference for all purposes.

FIELD OF THE INVENTION

The present invention relates to pyrimidine compounds and to their use in treating or preventing a respiratory syncytial virus (RSV) infection.

BACKGROUND TO THE INVENTION

RSV is a negative-sense, single-stranded RNA virus of the Paramyxoviridae family. RSV is readily transmitted by secretions from an infected person via surfaces or hand-to-hand transfer. Unlike influenza, it is not transmitted by small-particle aerosols. Following successful inoculation, the incubation period is between four and six days during which time the virus spreads from the nasopharynx to the lower respiratory tract by fusion of infected with uninfected cells and by sloughing of the necrotic epithelium. In infants, coupled with increased mucus secretion and oedema, this can lead to mucus plugging causing hyper-inflation and collapse of distal lung tissue indicative of bronchiolitis. Hypoxia is common and the ability to feed is often impaired because of respiratory distress. In RSV pneumonia, inflammatory infiltration of the airways consists of mononuclear cells and is more generalised, with involvement of the bronchioles, bronchi and alveoli. The duration and degree of viral shedding has been found to correlate with the clinical signs and severity of disease.

RSV is the leading cause of serious respiratory tract infections in infants and young children throughout the world. The highest morbidity and mortality occurs in those born prematurely and for those with chronic lung or heart disease, although many infants hospitalised for RSV infection are otherwise healthy. Severe RSV infection in infancy can lead to several years of recurrent wheezing and is linked to the later development of asthma.

RSV is also a major cause of morbidity and mortality in the elderly and in immunocompromised children and adults as well as those with chronic obstructive pulmonary disease (COPD) and congestive heart failure (CHF).

RSV has a seasonal incidence; it is highly predictable and occurs in the winters of both hemispheres, from September to May in Europe and North America, peaking in December and January, and can occur throughout the year in tropical countries. It affects >90% of infants and young children by the age of two years and as natural immunity is short-lived; many will be re-infected each year. As with influenza, in elderly people, RSV causes around 10% of winter hospitalisations with an associated mortality of 10%.

Current anti-RSV treatment involves the use of a monoclonal antibody to RSV, called palivizumab. Such use of palivizumab is a prophylactic, rather than therapeutic, treatment of RSV. Although this antibody is often effective, its use is restricted to preterm infants and infants at high risk. Indeed, its limited utility means that it is unavailable for many people in need of anti-RSV treatment. There is therefore an urgent need for effective alternatives to existing anti-RSV treatment.

Additionally, several compounds have been proposed as inhibitors of RSV, including benzimidazole-based compounds. For example, K D Combrink et al., Bioorganic & Medicinal Chemistry Letters, 17 (2007), 4784-4790 discloses the compound BMS-433771 and variants thereof. Further benzimidazole-based compounds are disclosed in WO-02/062290, WO-03/053344 and WO-10/103306.

WO 2013/068769 and WO2016/055780 disclose benzimidazole compounds having activity against RSV. However there exists a need to identify further compounds, and in particular compounds having favourable pharmacokinetic profiles.

SUMMARY OF THE INVENTION

It has now been found that a novel series of pyrimidine compounds are active as RSV inhibitors with favourable pharmacokinetics. Accordingly, the present invention provides a compound which is a pyrimidine of formula (I):

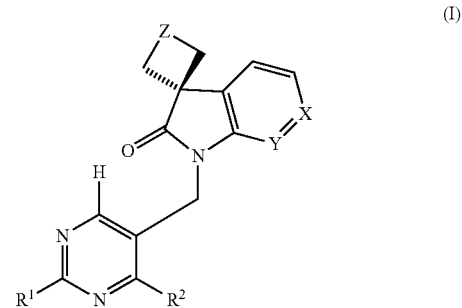

wherein:
Z is a direct bond or —(CH$_2$)$_n$— wherein n is 1 or 2;
one of X and Y is N, CH or CF, and the other of X and Y is CH;
one of R$^1$ and R$^2$ is selected from —NHR, —NR$_2$, —OR, —SR, —S(O)R, —S(O)$_2$R and a group of the following formula (A):

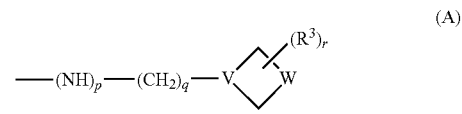

and the other of R$^1$ and R$^2$ is selected from —NHR', —OH, —OR' and a group of the above formula (A);
R is unsubstituted C$_1$-C$_6$ alkyl;
R' is a group selected from C$_1$-C$_6$ alkyl, 5- to 12-membered aryl and C$_3$-C$_6$ cycloalkyl, which group is unsubstituted or substituted;
W is —(CH$_2$)$_m$—, —CH$_2$—O—CH$_2$—, —CH$_2$—S—CH$_2$— or —CH$_2$—S(O)$_2$—CH$_2$—;
m is an integer of 1 to 4;
p is 1, q is an integer of 1-6 and V is N; or p is 1, q is 0 and V is CH; or p is 0, q is 0 and V is N;
r is 0 or 1; and
R$^3$ is —(CH$_2$)$_s$—NH$_2$ or —(CH$_2$)$_s$—OH wherein s is 0 or an integer of 1 to 4;
or a pharmaceutically acceptable salt thereof.

DETAILED DESCRIPTION OF THE INVENTION

When any group, ring, substituent or moiety defined herein is substituted, it is typically substituted by Q as defined below.

A C$_{1-6}$ alkyl group or moiety is linear or branched. A C$_{1-6}$ alkyl group is typically a C$_{1-4}$ alkyl group, or a C$_{4-6}$ alkyl group. Examples of C$_{1-6}$ alkyl groups and moieties include methyl, ethyl, n-propyl, i-propyl, n-butyl, i-butyl, t-butyl, n-pentyl, i-pentyl (i.e. 3-methylbut-1-yl), t-pentyl (i.e. 2-methylbut-2-yl), neopentyl (i.e. 2,2-dimethylpropan-1-yl), n-hexyl, i-hexyl (i.e. 4-methylpentan-1-yl), t-hexyl (i.e. 3-methylpentan-3-yl) and neopentyl (i.e. 3,3-dimethylbutan-1-yl). For the avoidance of doubt, where two alkyl moieties are present in a group, the alkyl moieties may be the same or different. A C$_{1-6}$ alkyl group is unsubstituted or substituted, typically by one or more groups Q as defined below. For example, a C$_{1-6}$ alkyl group is unsubstituted or substituted by 1, 2 or 3 groups Q as defined below.

Q is halo, nitro, —CN, OH, C$_{1-6}$ alkoxy, C$_{1-6}$ hydroxyalkyl, C$_{1-6}$ alkylthio, C$_{1-6}$ haloalkyl, C$_{1-4}$ haloalkoxy, —CO$_2$R''', —NR'''$_2$, —SR''', —S(=O)R''', —S(=O)$_2$R''', C$_3$-C$_{10}$ cycloalkyl, 5 to 10-membered heterocyclyl, 5- to 12-membered aryl or 5- to 12-membered heteroaryl, wherein each R''' is independently selected from H, C$_{1-6}$ alkyl, C$_{3-10}$ cycloalkyl, 5 to 10-membered heterocyclyl, 5- to 12-membered aryl and 5- to 12-membered heteroaryl.

A C$_{1-6}$ alkoxy group is linear or branched. It is typically a C$_{1-4}$ alkoxy group, for example a methoxy, ethoxy, propoxy, i-propoxy, n-propoxy, n-butoxy, sec-butoxy or tert-butoxy group. A C$_{1-6}$ alkoxy group is unsubstituted or substituted, typically by one or more groups Q as defined.

A C$_{1-6}$ alkylthio group is linear or branched. It is typically a C$_{1-4}$ alkylthio group, for example a methylthio, ethylthio, propylthio, i-propylthio, n-propylthio, n-butylthio, sec-butylthio or tert-butylthio group. A C$_{1-6}$ alkyltho group is unsubstituted or substituted, typically by one or more groups Q as defined.

A halogen or halo group is F, Cl, Br or I. Preferably it is F, Cl or Br. A C$_{1-6}$ alkyl group substituted by halogen may be denoted "C$_{1-6}$ haloalkyl", which means a C$_{1-6}$ alkyl group as defined above in which one or more hydrogens is replaced by halo. Likewise a C$_{1-6}$ alkoxy group substituted by halogen may be denoted "C$_{1-6}$ haloalkoxy", which means a C$_{1-6}$ alkoxy group as defined above in which one or more hydrogens is replaced by halo. Typically, C$_{1-6}$ haloalkyl or C$_{1-6}$ haloalkoxy is substituted by 1, 2 or 3 said halogen atoms. Haloalkyl and haloalkoxy groups include perhaloalkyl and perhaloalkoxy groups such as —CX$_3$ and —OCX$_3$ wherein X is a halogen, for example —CF$_3$— CCl$_3$—OCF$_3$ and —OCCl$_3$.

A C$_{1-6}$ hydroxyalkyl group is a C$_{1-6}$ alkyl group as defined above, substituted by one or more OH groups. Typically, it is substituted by one, two or three OH groups. Preferably, it is substituted by a single OH group.

A 5- to 12-membered aryl group is an aromatic carbocyclic group containing from 5 to 12 carbon atoms, for instance from 6 to 10 carbon atoms, such as 6 or 10 carbon atoms. It is monocyclic or a fused bicyclic ring system in which an aromatic ring is fused to another aromatic carbocyclic ring. Examples of a 5- to 12-membered aryl group include phenyl and naphthyl. When substituted, an aryl group is typically substituted by C$_{1-4}$ alkyl or a group Q as defined above, for instance by 1, 2 or 3, groups selected from a C$_{1-4}$ alkyl group and a group Q as defined above.

A C$_{3-10}$ cycloalkyl group is a saturated hydrocarbon ring having from 3 to 10 carbon atoms. A C$_{3-10}$ cycloalkyl group may be, for instance, C$_3$-C$_7$ cycloalkyl such as cyclopropyl, cyclobutyl, cyclopentyl, cyclohexyl, or cycloheptyl. Typically it is C$_3$-C$_6$ cycloalkyl, or C$_4$-C$_6$ cycloalkyl, for example cyclobutyl, cyclopentyl or cyclohexyl. In one embodiment it is cyclobutyl. A C$_{3-10}$ cycloalkyl group is unsubstituted or substituted, typically by one or more groups Q as defined above.

A 5- to 12-membered heteroaryl group or moiety is a 5- to 12-membered aromatic heterocyclic group which contains 1, 2, 3, or 4 heteroatoms selected from O, N and S. It is monocyclic or bicyclic. Typically it contains one N atom and 0, 1, 2 or 3 additional heteroatoms selected from O, S and N. It may be, for example, a 5- to 7-membered heteroaryl group, for instance a 5- or 6-membered N-containing heteroaryl group. Examples include pyridyl, pyrazinyl, pyrimidinyl, pyridazinyl, furanyl, thienyl, pyrazolidinyl, pyrrolyl, oxadiazolyl, oxazolyl, isoxazolyl, thiazolyl, thiadiazolyl, imidazolyl and pyrazolyl groups. Furanyl, thienyl, pyridyl and pyrimidyl groups are preferred. When substituted, a heteroaryl group is typically substituted by one or more, e.g. 1, 2 or 3, groups selected from C$_{1-4}$ alkyl and a group Q as defined above.

A 5- to 10-membered heterocyclyl moiety is a monocyclic or bicyclic non-aromatic, saturated or unsaturated C$_{5-10}$ carbocyclic ring, in which at least one, for example 1, 2 or 3, carbon atoms in the ring are replaced with an atom or group selected from O, S, SO, SO$_2$, CO and N. Typically, it is a saturated C$_{5-10}$ ring in which 1, 2 or 3 of the carbon atoms in the ring are replaced with an atom or group selected from O, S, SO$_2$, CO and NH. More typically it is a monocyclic ring, preferably a monocyclic C$_5$-C$_6$ ring. Examples include piperidyl, piperidin-2,6-dionyl, piperidin-2-onyl, piperazinyl, morpholinyl, thiomorpholinyl, S,S-dioxothiomorpholinyl, 1,3-dioxolanyl, pyrrolidinyl, imidazol-2-onyl, pyrrolidin-2-onyl, tetrahydrofuranyl and tetrahydropyranyl moieties.

For the avoidance of doubt, although the above definitions of heteroaryl and heterocyclyl groups refer to an "N" atom which can be present in the ring, as will be evident to a skilled chemist the N atom will be protonated (or will carry a substituent as defined above) if it is attached to each of the adjacent ring atoms via a single bond. Such protonated forms are embraced within the present definitions of heteroaryl and heterocyclyl groups.

In the pyrimidines of formula (I), Z is a direct bond or —(CH$_2$)$_n$— wherein n is 1 or 2. In one embodiment Z is a direct bond.

In formula (I), one of X and Y is N, CH or CF and the other is CH. Typically, one of X and Y is N or CF and the other is CH. In one embodiment X is CF and Y is CH. In another embodiment X is N and Y is CH.

One of R$^1$ and R$^2$ is selected from —NHR, —NR$_2$, —OR, —SR, —S(O)R, —S(O)$_2$R and a group of the following formula (A):

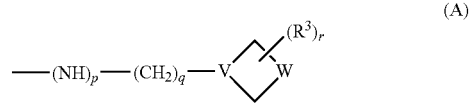

(A)

and the other of $R^1$ and $R^2$ is selected from —NHR', —OH, —OR' and a group of the above formula (A), wherein R, p, q, V, W, $R^3$, r and W are all as defined above. In one embodiment at least one of $R^1$ and $R^2$ is a group of formula (A). In another embodiment each of $R^1$ and $R^2$ is a group of formula (A).

The group R' may be $C_1$-$C_6$ alkyl, for instance $C_1$-$C_4$ alkyl. Alternatively it is 5- to 12-membered aryl, for instance phenyl; or $C_3$-$C_6$ cycloalkyl, for instance $C_4$-$C_6$ alkyl. The group R' is unsubstituted or substituted. When substituted it is typically substituted by R, —OH, —OR, —$CF_3$, —$S(O)_2R$, —CN, —$NH_2$, —NHR or $NR_2$, wherein R is as defined above.

W is selected from —$(CH_2)_m$—, —$CH_2$—O—$CH_2$—, —$CH_2$—S—$CH_2$— and —$CH_2$—$S(O)_2$—$CH_2$—, wherein m is an integer of 1 to 4. Typically W is selected from —$(CH_2)_m$—, —$CH_2$—O—$CH_2$— and —$CH_2$—$S(O)_2$—$CH_2$—.

When W is —$(CH_2)_m$— and V is CH, the ring formed by V, W and the two C atoms to which V and W are attached is cyclobutyl, cyclopentyl, cyclohexyl or cycloheptyl and is optionally substituted by $R^3$ as defined above. In these embodiments p is 1 and q is 0.

When W is —$(CH_2)_m$— and V is N, the ring formed by V, W and the two C atoms to which V and W are attached is azetidinyl, pyrrolidinyl, piperidinyl or azepanyl and is optionally substituted by $R^3$ as defined above. In these embodiments p is 1 and q is an integer of 1 to 6, typically 1 to 3, more typically 1. Alternatively, in these embodiments, p and q are both 0.

When W is —$CH_2$—O—$CH_2$— and V is N, the ring formed by V, W and the two C atoms to which V and W are attached is morpholinyl. When W is —$CH_2$—O—$CH_2$— and V is CH, the ring formed by V, W and the two C atoms to which V and W are attached is pyranyl.

In the group of formula (A) p is 1, q is an integer of 1-6, for instance 1-3, and V is N; or p is 1, q is 0 and V is CH; or p is 0, q is 0 and V is N. In one embodiment p is 1, q is 1 or 2 and V is N.

Examples of the group of formula (A) include the following structures:

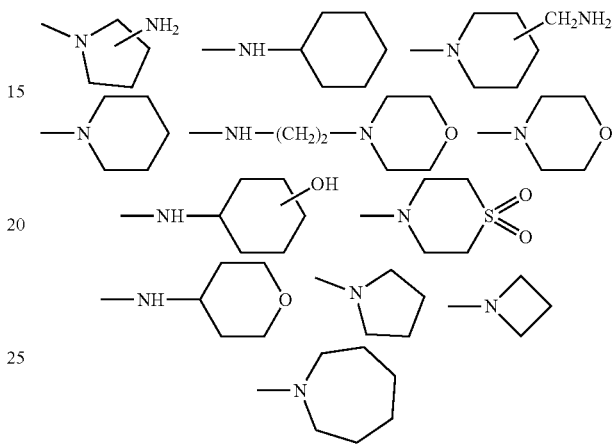

Specific compounds of the invention include those shown in the following table:

| No | Structure | Name |
|---|---|---|
| 1 | 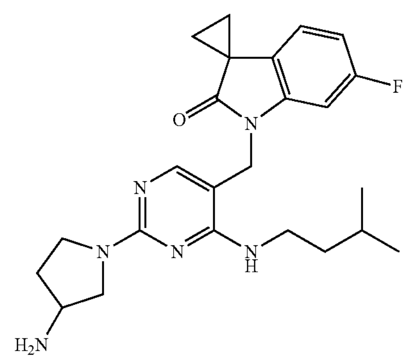 [SMILES: CC(C)CCNc1nc(N2CCC(N)C2)ncc1CN1C(=O)C2(CC2)c2ccc(F)cc21] | 1'-((2-(3-Aminopyrrolidin-1-yl)-4-(isopentylamino)pyrimidin-5-yl)methyl)-6'-fluorospiro[cyclopropane-1,3'-indolin]-2'-one |
| 2 | 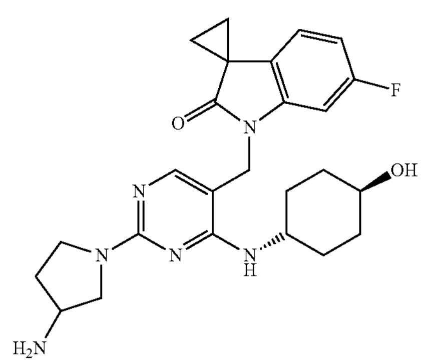 | 1'-((2-(3-Aminopyrrolidin-1-yl)-4-(((1r,4r)-4-hydroxycyclohexyl)amino)pyrimidin-5-yl)methyl)-6'-fluorospiro[cyclopropane-1,3'-indolin]-2'-one |

-continued

| No | Structure | Name |
|---|---|---|
| 3 | 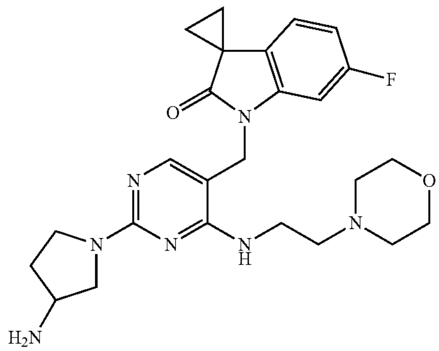 [SMILES: NC1CCN(c2ncc(CN3C(=O)C4(CC4)c4ccc(F)cc43)c(NCCN3CCOCC3)n2)C1] | 1'-((2-(3-Aminopyrrolidin-1-yl)-4-((2-morpholinoethyl)amino)pyrimidin-5-yl)methyl)-6'-fluorospiro[cyclopropane-1,3'-indolin]-2'-one |
| 4 | 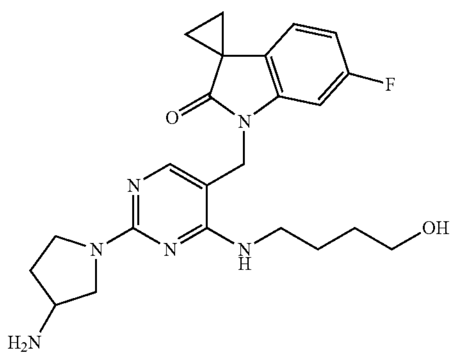 | 1'-((2-(3-Aminopyrrolidin-1-yl)-4-((4-hydroxybutyl)amino)pyrimidin-5-yl)methyl)-6'-fluorospiro[cyclopropane-1,3'-indolin]-2'-one |
| 5 | 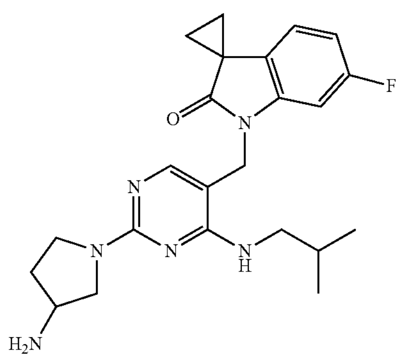 [SMILES: CC(C)CNc1nc(N2CCC(N)C2)ncc1CN1C(=O)C2(CC2)c2ccc(F)cc21] | 1'-((2-(3-Aminopyrrolidin-1-yl)-4-(isobutylamino)pyrimidin-5-yl)methyl)-6'-fluorospiro[cyclopropane-1,3'-indolin]-2'-one |
| 6 | 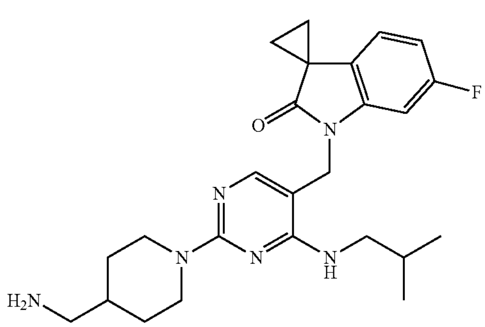 [SMILES: CC(C)CNc1nc(N2CCC(CN)CC2)ncc1CN1C(=O)C2(CC2)c2ccc(F)cc21] | 1'-((2-(4-Aminomethyl)piperidin-1-yl)-4-(isobutylamino)pyrimidin-5-yl)methyl)-6'-fluorospiro[cyclopropane-1,3'-indolin]-2'-one |

| No | Structure | Name |
|---|---|---|
| 7 | 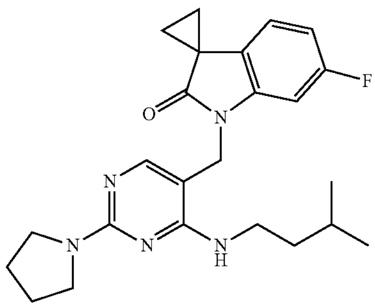 [SMILES: CC(C)CCNc1nc(N2CCCC2)ncc1CN1C(=O)C2(CC2)c2ccc(F)cc21] | 6'-Fluoro-1'-((4-(isopentylamino)-2-(pyrrolidin-1-yl)pyrimidin-5-yl)methyl)spiro[cyclopropane-1,3'-indolin]-2'-one |
| 8 | 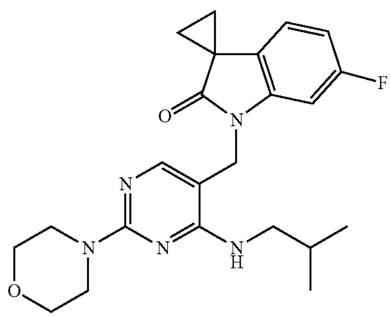 [SMILES: CC(C)CNc1nc(N2CCOCC2)ncc1CN1C(=O)C2(CC2)c2ccc(F)cc21] | 6'-Fluoro-1'-((4-(isobutylamino)-2-morpholinopyrimidin-5-yl)methyl)spiro[cyclopropane-1,3'-indolin]-2'-one |
| 9 | 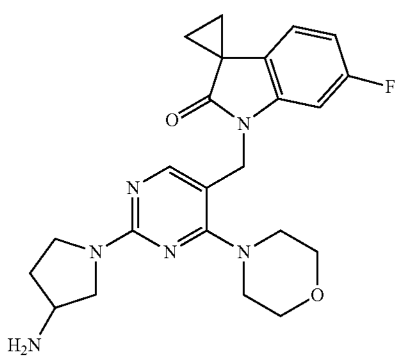 [SMILES: NC1CCN(c2ncc(CN3C(=O)C4(CC4)c4ccc(F)cc43)c(N3CCOCC3)n2)C1] | 1'-((2-(3-Aminopyrrolidin-1-yl)-4-morpholinopyrimidin-5-yl)methyl)-6'-fluorospiro[cyclopropane-1,3'-indolin]-2'-one |
| 10 | 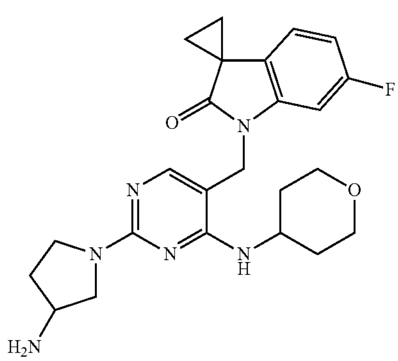 [SMILES: NC1CCN(c2ncc(CN3C(=O)C4(CC4)c4ccc(F)cc43)c(NC3CCOCC3)n2)C1] | 1'-((2-(3-Aminopyrrolidin-1-yl)-4-((3-methoxypropyl)amino)pyrimidin-5-yl)methyl)-6'-fluorospiro[cyclopropane-1,3'-indolin]-2'-one |

-continued

| No | Structure | Name |
|---|---|---|
| 11 | 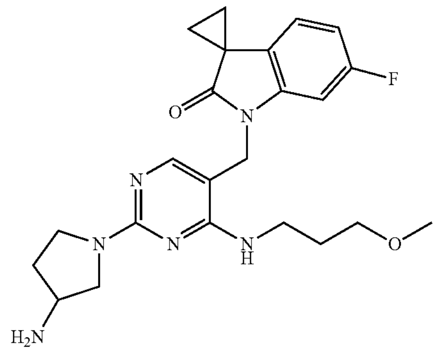 [SMILES: COCCCNc1nc(N2CCC(N)C2)ncc1CN1C(=O)C2(CC2)c2ccc(F)cc21] | 1'-((2-(3-Aminopyrrolidin-1-yl)-4-((3-methoxypropyl)amino)pyrimidin-5-yl)methyl)-6'-fluorospiro[cyclopropane-1,3'-indolin]-2'-one |
| 12 | 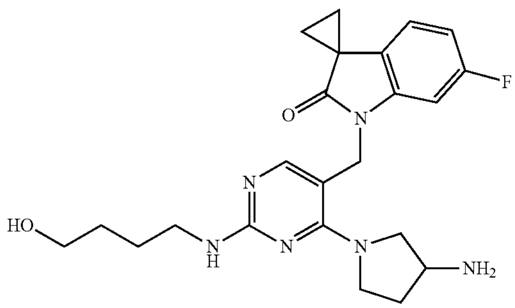 [SMILES: NC1CCN(c2nc(NCCCCO)ncc2CN2C(=O)C3(CC3)c3ccc(F)cc32)C1] | 1'-((4-(3-Aminopyrrolidin-1-yl)-2-((4-hydroxybutyl)amino)pyrimidin-5-yl)methyl)-6'-fluorospiro[cyclopropane-1,3'-indolin]-2'-one |
| 13 | 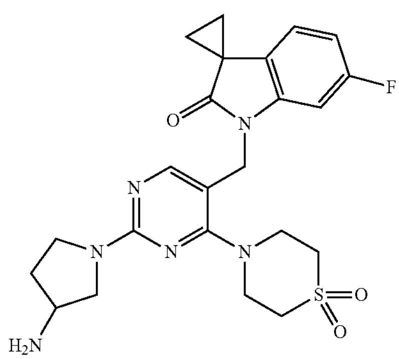 [SMILES: NC1CCN(c2ncc(CN3C(=O)C4(CC4)c4ccc(F)cc43)c(N3CCS(=O)(=O)CC3)n2)C1] | 1'-((2-(3-Aminopyrrolidin-1-yl)-4-(1,1-dioxidothiomorpholino)pyrimidin-5-yl)methyl)-6'-fluorospiro[cyclopropane-1,3'-indolin]-2'-one |
| 14 | 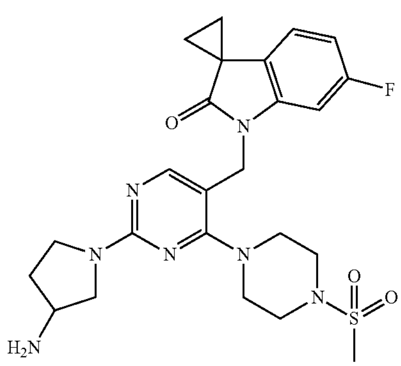 [SMILES: CS(=O)(=O)N1CCN(c2nc(N3CCC(N)C3)ncc2CN2C(=O)C3(CC3)c3ccc(F)cc32)CC1] | 1'-{[2-(3-Aminopyrrolidin-1-yl)-4-(4-methanesulfonylpiperazin-1-yl)pyrimidin-5-yl]methyl}-6'-fluoro-1',2' dihydrospiro[cyclopropane-1,3'-indole]-2'-one |

-continued

| No | Structure | Name |
|----|-----------|------|
| 15 | 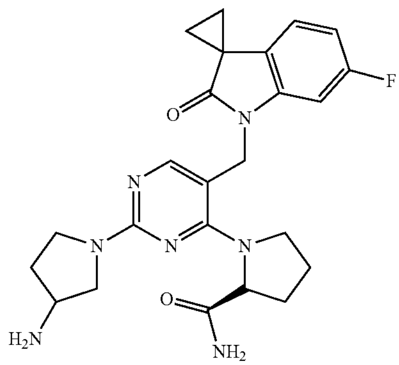 | 1-[2-(3-Aminopyrrolidin-1-yl)-5-({6'-fluoro-2'-oxo-1',2'-dihydrospiro[cyclopropane-1,3'-indole]-1'-yl}methyl)pyrimidin-4-yl]pyrrolidine-2-carboxamide |
| 16 | 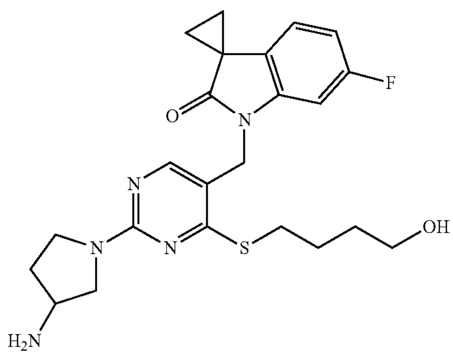 [SMILES: NC1CCN(c2ncc(CN3C(=O)C4(CC4)c4ccc(F)cc43)c(SCCCCO)n2)C1] | 1'-{[2-(3-Aminopyrrolidin-1-yl)-4-[(4-hydroxybutyl)sulfanyl]pyrimidin-5-yl]methyl}-6'-fluoro-1',2'-dihydrospiro[cyclopropane-1,3'-indole]-2'-one |
| 17 | 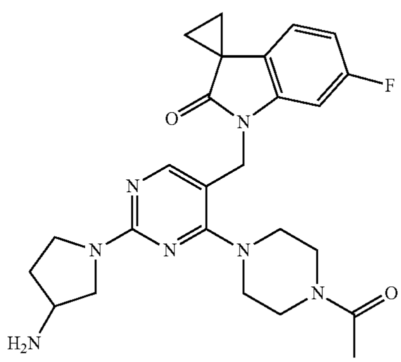 [SMILES: CC(=O)N1CCN(c2nc(N3CCC(N)C3)ncc2CN2C(=O)C3(CC3)c3ccc(F)cc32)CC1] | 1'-{[4-(4-Acetylpiperazin-1-yl)-2-(3-aminopyrrolidin-1-yl)pyrimidin-5-yl]methyl}-6'-fluoro-1',2'-dihydrospiro[cyclopropane-1,3'-indole]-2'-one |
| 18 | 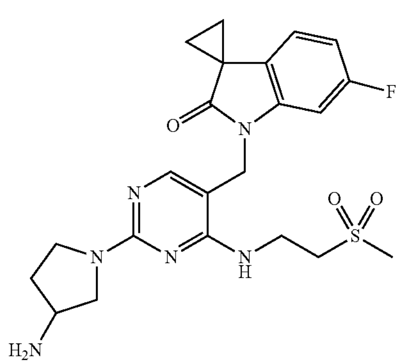 [SMILES: CS(=O)(=O)CCNc1nc(N2CCC(N)C2)ncc1CN1C(=O)C2(CC2)c2ccc(F)cc21] | 1'-{[2-(3-Aminopyrrolidin-1-yl)-4-[(2-methanesulfonylethyl)amino]pyrimidin-5-yl]methyl}-6'-fluoro-1',2'-dihydrospiro[cyclopropane-1,3'-indole]-2'-one |

-continued

| No | Structure | Name |
|---|---|---|
| 19 | 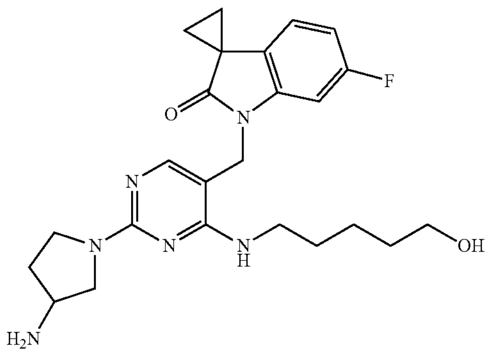 [SMILES: NC1CCN(c2ncc(CN3C(=O)C4(CC4)c4ccc(F)cc43)c(NCCCCCO)n2)C1] | 1'-{[2-(3-Aminopyrrolidin-1-yl)-4-[(5-hydroxypentyl)amino]pyrimidin-5-yl]methyl}-6'-fluoro-1',2'-dihydrospiro[cyclopropane-1,3'-indole]-2'-one |
| 20 | 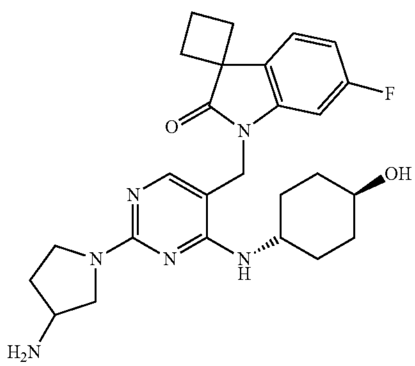 | 1'-{[2-(3-Aminopyrrolidin-1-yl)-4-[(4-hydroxycyclohexyl)amino]pyrimidin-5-yl]methyl}-6'-fluoro-1',2'-dihydrospiro[cyclobutane-1,3'-indole]-2'-one |
| 21 | 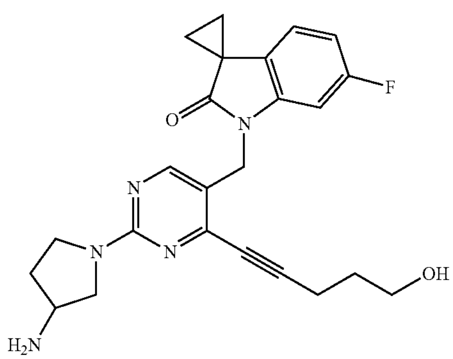 [SMILES: NC1CCN(c2ncc(CN3C(=O)C4(CC4)c4ccc(F)cc43)c(C#CCCCO)n2)C1] | 1'-{[2-(3-Aminopyrrolidin-1-yl)-4-(5-hydroxypent-1-yn-1-yl)pyrimidin-5-yl]methyl}-6'-fluoro-1',2'-dihydrospiro[cyclopropane-1,3'-indole]-2'-one |
| 22 | 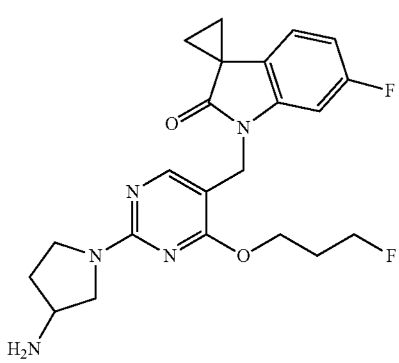 [SMILES: NC1CCN(c2ncc(CN3C(=O)C4(CC4)c4ccc(F)cc43)c(OCCCF)n2)C1] | 1'-{[2-(3-Aminopyrrolidin-1-yl)-4-(3-fluoropropoxy)pyrimidin-5-yl]methyl}-6'-fluoro-1',2'-dihydrospiro[cyclopropane-1,3'-indole]-2'-one |

-continued

| No | Structure | Name |
|---|---|---|
| 23 | 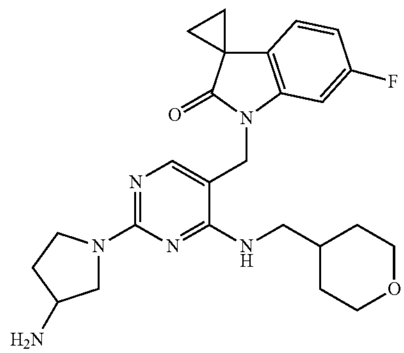 [SMILES: NC1CCN(c2ncc(CN3C(=O)C4(CC4)c4ccc(F)cc43)c(NCC3CCOCC3)n2)C1] | 1'-{[2-(3-Aminopyrrolidin-1-yl)-4-{[(oxan-4-yl)methyl]amino}pyrimidin-5-yl]methyl}-6'-fluoro-1',2'-dihydrospiro[cyclopropane-1,3'-indole]-2'-one |
| 24 | 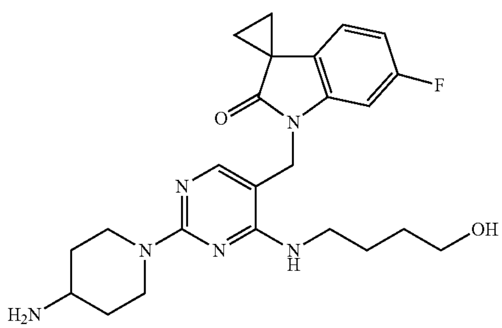 [SMILES: NC1CCN(c2ncc(CN3C(=O)C4(CC4)c4ccc(F)cc43)c(NCCCCO)n2)CC1] | 1'-{[2-(4-Aminopiperidin-1-yl)-4-[(4-hydroxybutyl)amino]pyrimidin-5-yl]methyl}-6'-fluoro-1',2'-dihydrospiro[cyclopropane-1,3'-indole]-2'-one |
| 25 | 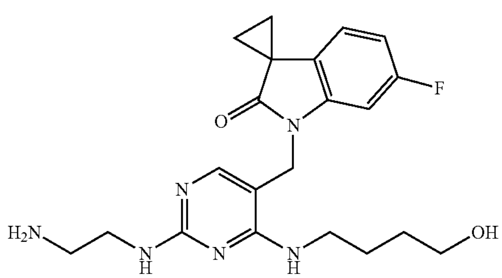 [SMILES: NCCNc1ncc(CN2C(=O)C3(CC3)c3ccc(F)cc32)c(NCCCCO)n1] | 1'-({2-[(2-Aminoethyl)amino]-4-[(4-hydroxybutyl)amino]pyrimidin-5-yl}methyl)-6'-fluoro-1',2'-dihydrospiro[cyclopropane-1,3'-indole]-2'-one |
| 26 | 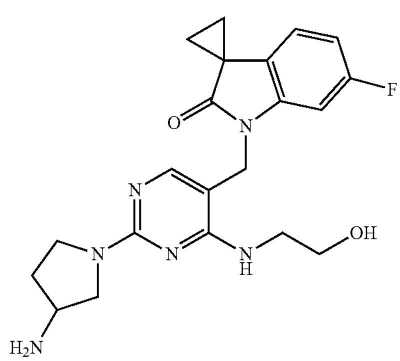 [SMILES: NC1CCN(c2ncc(CN3C(=O)C4(CC4)c4ccc(F)cc43)c(NCCO)n2)C1] | 1'-{[2-(3-Aminopyrrolidin-1-yl)-4-[(2-hydroxyethyl)amino]pyrimidin-5-yl]methyl}-6'-fluoro-1',2'-dihydrospiro[cyclopropane-1,3'-indole]-2'-one |

| No | Structure | Name |
|---|---|---|
| 27 | 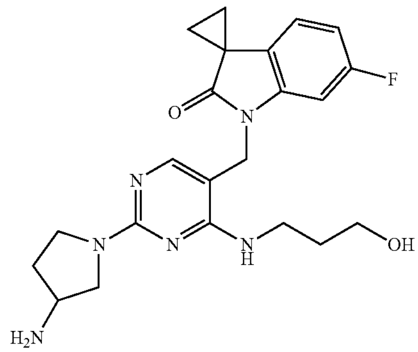 [SMILES: NC1CCN(c2ncc(CN3C(=O)C4(CC4)c4ccc(F)cc43)c(NCCCO)n2)C1] | 1'-{[2-(3-Aminopyrrolidin-1-yl)-4-[(3-hydroxypropyl)amino]pyrimidin-5-yl]methyl}-6'-fluoro-1',2'-dihydrospiro[cyclopropane-1,3'-indole]-2'-one |
| 28 | 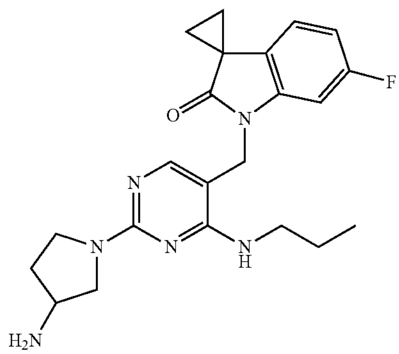 [SMILES: CCCNc1nc(N2CCC(N)C2)ncc1CN1C(=O)C2(CC2)c2ccc(F)cc21] | 1'-{[2-(3-Aminopyrrolidin-1-yl)-4-(propylamino)pyrimidin-5-yl]methyl}-6'-fluoro-1',2'-dihydrospiro[cyclopropane-1,3'-indole]-2'-one |
| 29 | | 1'-{[2-(3-Aminopyrrolidin-1-yl)-4-(ethylamino)pyrimidin-5-yl]methyl}-6'-fluoro-1',2'-dihydrospiro[cyclopropane-1,3'-indole]-2'-one | and the pharmaceutically acceptable salts thereof.

The compounds of the invention may contain asymmetric or chiral centres, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Compounds of Formula (I) containing one or more chiral centre may be used in enantiomerically or diastereoisomerically pure form, or in the form of a mixture of isomers.

The present invention embraces all geometric and positional isomers of compounds of the invention as defined above. For example, if a compound of the invention incorporates a double bond or a fused ring, the cis- and trans-forms, as well as mixtures thereof, are embraced within the scope of the invention. Both the single positional isomers and mixture of positional isomers are also within the scope of the present invention.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol tautomerizations. Valence tautomers include interconversions by reorganization of some of the bonding electrons.

Compounds of the invention can be prepared by synthetic methods described in the Examples that follow, or by analogy with such methods.

A pyrimidine of formula (I) can be converted into a pharmaceutically acceptable salt thereof, and a salt can be converted into the free compound, by conventional methods. For instance, a pyrimidine of formula (I) can be contacted with a pharmaceutically acceptable acid to form a pharmaceutically acceptable salt. A pharmaceutically acceptable salt is a salt with a pharmaceutically acceptable acid or base.

Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Compounds of the present invention have been found in biological tests to be inhibitors of respiratory syncytial virus (RSV). The compounds are therefore therapeutically useful. Accordingly, the present invention further provides a compound which is a pyrimidine of formula (I), as defined above, or a pharmaceutically acceptable salt thereof, for use in a method of treating the human or animal body by therapy. The invention also provides a compound of the invention as defined above for use in a method treating or preventing an RSV infection. Still further, the present invention provides the use of a compound of the invention as defined above in the manufacture of a medicament for use in treating or preventing an RSV infection. A subject suffering from or susceptible to an RSV infection may thus be treated by a method comprising the administration thereto of a compound of the invention as defined above. The condition of the subject may thereby be improved or ameliorated.

The RSV infection is typically a respiratory tract infection. The RSV infection may be an infection in a child, for instance a child under ten years of age or an infant under two years of age. In one embodiment the invention provides a compound as defined above for use in treating or preventing an RSV infection in paediatric patients. Alternatively the infection may be an infection in a mature or elderly adult, for instance an adult over 60 years of age, an adult over 70 years of age, or an adult over 80 years of age. The invention further provides a compound for use in treating or preventing an RSV infection in geriatric patients.

The RSV infection may be an infection in an immunocompromised individual or an individual suffering from COPD or CHF. In another embodiment, the RSV infection is an infection in a non-compromised individual, for instance an individual who is otherwise healthy.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection, infusion, or by inhalation or nebulaisation. The compound is preferably given by oral administration.

The dosage depends on a variety of factors including the age, weight and condition of the patient and the route of administration. Daily dosages can vary within wide limits and will be adjusted to the individual requirements in each particular. Typically, however, the dosage adopted for each route of administration when a compound is administered alone to adult humans is 0.0001 to 650 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A unit dose form such as a tablet or a capsule will usually contain 1-250 mg of active ingredient. For example, a compound of formula (I) could be administered to a human patient at a dose of between 100-250 mg either once a day, twice or three times a day. For example, a compound of formula (I) could be administered to a human patient at a dose of between 100-250 mg either once a day, twice or three times a day.

The compounds of formula (I) and pharmaceutically acceptable salts thereof may be used on their own. Alternatively, they may be administered in the form of a pharmaceutical composition. The present invention therefore also provides a pharmaceutical composition comprising a compound of formula (I) or a pharmaceutically acceptable salt thereof as hereinbefore defined, in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The compounds of the invention may be administered in a variety of dosage forms. Thus, they can be administered orally, for example as tablets, troches, lozenges, aqueous or oily suspensions, solutions, dispersible powders or granules. The compounds of the invention may also be administered parenterally, whether subcutaneously, intravenously, intramuscularly, intrasternally, transdermally, by infusion techniques or by inhalation or nebulisation. The compounds may also be administered as suppositories.

Solid oral forms of the pharmaceutical composition of the invention may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulfates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. Further suitable carriers for suspensions include sterile water, hydroxypropylmethyl cellulose (HPMC), polysorbate 80, polyvinylpyrrolidone (PVP), aerosol AOT (i.e. sodium 1,2-bis(2-ethylhexoxycarbonyl)ethanesulphonate), pluronic F127 and/or captisol (i.e. sulfobutylether-beta-cyclodextrin).

The compounds of the invention may, for example, be formulated as aqueous suspensions in a carrier selected from:
(i) 0.5% w/v hydroxypropylmethyl cellulose (HPMC)/0.1% w/v polysorbate 80;
(ii) 0.67% w/v polyvinylpyrrolidone (PVP)/0.33% w/v aerosol AOT (sodium 1,2-bis(2-ethylhexoxycarbonyl)ethanesulphonate);
(iii) 1% w/v pluronic F 127; and
(iv) 0.5% w/v polysorbate 80.

The carriers may be prepared by standard procedures known to those of skill in the art. For example, each of the carriers (i) to (iv) may be prepared by weighing the required amount of excipient into a suitable vessel, adding approximately 80% of the final volume of water and magnetically stirring until a solution is formed. The carrier is then made up to volume with water. The aqueous suspensions of compounds of formula I may be prepared by weighing the required amount of a compound of formula I into a suitable vessel, adding 100% of the required volume of carrier and magnetically stirring.

Solutions for injection or infusion may contain as carrier, for example, sterile water or preferably they may be in the form of sterile, aqueous, isotonic saline solutions.

The compounds of the invention may also be administered in conjunction with other compounds used for the treatment of viral infections. Thus, the invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment or prevention of a viral infection, particularly infection by RSV.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

Suitable therapeutic agents for use in the combination therapies include
(i) RSV nucleocapsid (N)-protein inhibitors;
(ii) other RSV protein inhibitors, such as those that inhibit the phosphoprotein (P) protein and large (L) protein;
(iii) anti-RSV monoclonal antibodies, such as the F-protein antibodies;
(iv) immunomodulating toll-like receptor compounds;
(v) other respiratory virus anti-virals, such as anti-influenza and anti-rhinovirus compounds; and/or
(vi) anti-inflammatory compounds.

The RSV nucleocapsid (N)-protein plays a pivotal role in viral transcription and replication, mediating the interaction between the genomic RNA and the virally encoded RNA-dependent RNA polymerase. The RSV P- and L-proteins are components of RSV's virally encoded RNA-dependent RNA polymerase.

According to a further aspect of the invention, there is provided a compound of the formula (I) or a pharmaceutically acceptable salt thereof as hereinbefore defined in combination with one or more of the therapeutic agents listed as (i) to (vi) above for use in the treatment of RSV.

The following Examples illustrate the invention. They do not however, limit the invention in any way.

EXAMPLES

All temperatures are in ° C. Melting points were determined in open capillaries, using a Stuart SMP30 digital melting point apparatus and are uncorrected. NMR spectra were recorded on a Bruker Avance-III-400 (1H=400.06 MHz; 19F=376.4 MHz; 13C=100.6 MHz) at ambient probe temperature (nominal 295K) using either deuterated chloroform (CDCl$_3$) or hexadeuterated dimethylsulphoxide (DMSO-d6) as solvents. Chemical shifts ($\delta$) are given in ppm vs. TMS ($^1$H NMR, $^{13}$C NMR) as an internal reference. Coupling constants are given in Hertz (Hz). CI MS (positive ion) was performed on an Advion expression$^L$ compact mass spectrometer using the TLC plate express reader. Silica gel plates, Supelco. S-A (Fluorescence Indicator at 254 nM) (Sigma-Aldrich Chemie GmbH Riedstr. 2D-8955T, Steinheim 497329-970, Germany) were used for TLC monitoring.

Additional liquid chromatography mass spectra were acquired on a QToF Premier mass spectrometer equipped with an Acquity UPLC (Waters Corp.). The LC separation was achieved on a C18 BEH chromatography column (2.1 mm×100 mm and 1.7 um particle size) using a reverse phase gradient of 100% aqueous (0.1% formic acid in water) to 100% organic (0.1% formic acid in acetonitrile) at 0.6 mL/min. Column chromatography was performed using silica gel (70-230 mesh) from Sigma-Aldrich (The Old Brickyard, Gillingham, SP8 4JL. UK) or using a Biotage Isolera One system using KP-Sil, Ultra or NH columns. Microwave synthesis was performed using a Milestone microSYNTH MA020 advanced microwave synthesis lab station with a T640 terminal controller. The energy output was 500 watts and the heating programs included a 6-minute temperature ramp and 10-minute cool down.

Reagents were obtained from Sigma-Aldrich, Fluorochem and Alfa Aesar and were used without further purification.

Abbreviations

DCM: Dichloromethane
DIAD Diisopropyl azodicarboxylate
DIPEA: N,N-Di-isopropylethylamine
DME: 1,2-Dimethoxyethane
DMF: N,N-Dimethylformamide
DMSO: Dimethyl sulphoxide
EtOAc Ethyl acetate
EtOH Ethanol
HATU: O-(7-Azabenzotriazol-1-yl)-N,N,N',N'-tetramethyluronium hexafluorophosphate
HBTU: O-(Benzotriazol-1-yl)-N,N,N',N'-tetramethyluronium hexafluorophosphate
HMDS Hexamethyldisilazane
mCPBA meta-Chloroperoxybenzoic acid
MeCN Acetonitrile
MeOH Methanol
NMM: N-Methylmorpholine
Pd$_2$(dba)$_3$ Tris(dibenzylideneacetone)dipalladium(0)
rt: room temperature
TBTU O-(Benzotriazol-1-yl)-N,N,N',N'-tetramethyluronium tetrafluoroborate TFA Trifluoroacetic acid
THF Tetrahydrofuran
TMEDA N,N,N',N'-tetramethylethylenediamine Preparatory Example 1

5-(Hydroxymethyl)pyrimidine-2,4(1H, 3H)-dione

Uracil (10.0 g, 89.2 mmol, 1.0 eq.) and paraformaldehyde (3.24 g, 107 mmol, 1.2 eq.) were treated with KOH (0.5 M, 133 ml) and the mixture heated at 50° C. for 8 hours 30 minutes, stirred at rt for 64 hours then heated at 50° C. for 24 hours. The mixture was cooled to 0° C. in an ice bath and acidified to pH 6 with HCl (conc). The precipitate was filtered off, washed with water and oven dried providing the title compound (4.93 g, 39%) as a white solid.
$^1$H NMR (400 MHz, DMSO) δ 11.05 (s, 1H), 10.71 (s, 1H), 7.24 (s, 1H), 4.85 (t, J=5.5 Hz, 1H), 4.11 (dd, J=5.5, 1.1 Hz, 2H). $R_f$=0.10 (50:8:1 DCM:EtOH:NH$_3$)

Preparatory Example 2

2,4-Dichloro-5-(chloromethyl)pyrimidine 5-(Hydroxymethyl)pyrimidine-2,4(1H,3H)-dione from Preparatory Example 1 (5.53 g, 38.9 mmol, 1 eq.) was treated with Phosphorus(V) oxychloride (27.2 ml, 292 mmol, 7.5 eq.), followed by the dropwise addition of DIPEA (25.8 ml, 156 mmol, 4 eq.). Toluene (5.7 ml) was added to the resulting suspension, and the mixture heated to 110° C. for 19 hours. Phosphorus(V) oxychloride was removed under reduced pressure and the residue was poured into HCl (1.5 M, 125 ml), allowed to cool to rt and extracted with EtOAc (2×50 ml), washed successively with water (50 ml), NaHCO$_3$ (50 ml of a saturated solution) and brine (50 ml). The organics were dried over MgSO$_4$, filtered, concentrated under reduced pressure and purified by column chromatography (1:1 petrol:EtOAc) providing the title compound (6.07 g, 79%) as an orange oil.

Preparatory Example 3

2,4-Dichloro-5-(iodomethyl)pyrimidine

To a solution of (2,4-dichloro-5-iodomethyl)pyrimidine from Preparatory Example 2 (6.07 g, 30.4 mmol, 1 eq.) in acetone (30 ml) was added sodium iodide (7.27 g, 30.4 mmol, 1 eq.) and the resulting mixture stirred at rt for 1 hour then heated to reflux and stirred for a further 30 minutes. The resulting mixture was cooled to rt and the precipitate filtered off. The filtrate was evaporated under reduced pressure and the residue taken into diethyl ether (200 ml). The organics were successively washed with sodium metabisulfite (50 ml of a saturated solution), water (50 ml) and brine (50 ml), dried over MgSO$_4$, filtered and concentrated under reduced pressure to afford the title compound (7.35 g, 84%).
$^1$H NMR (400 MHz, DMSO) δ 8.62 (s, 1H), 4.41 (s, 2H); $R_f$=0.68 (1:1 Petroleum ether:EtOAc)

Preparatory Example 4

1'-((2,4-Dichloropyrimidin-5-yl)methyl)-6'-fluorospiro[cyclopropane-1,3'-indolin]-2'-one 2,4-Dichloro-5-(iodomethyl)pyrimidine from Preparatory Example 3 (1.73 g, 5.98 mmol, 1 eq.), 6'-fluorospiro[cyclopropane-1,3'-indolin]-2'-one (1.06 g, 5.98 mmol, 1 eq.) and K$_2$CO$_3$ (2.03 g, 14.7 mmol, 2.45 eq.) in MeCN (50 ml) were heated to reflux for 5 hours. The mixture was allowed to cool to rt and MeCN was removed under reduced pressure. The residue was partitioned between DCM (50 ml) and water (50 ml). The organic layer was successively washed with water (25 ml) and brine (25 ml), dried over MgSO$_4$, filtered and concentrated under reduced pressure. The residual solid was purified by column chromatography (400:8:1 DCM:EtOH: NH$_3$) to afford the title compound (1.44 g, 71%) as a light brown solid.
$^1$H NMR (400 MHz, DMSO) δ 8.56 (s, 1H), 7.11-7.07 (m, 2H), 6.88-6.82 (m, 2H), 5.06 (s, 2H), 1.71-1.67 (m, 2H), 1.60-1.56 (m, 2H); MS CI 339.8 [M+H]$^+$ Preparatory Example 5

1'-((2-Chloro-4-(isopentylamino)pyrimidin-5-yl)methyl)-6'-fluorospiro[cyclopropane-1,3'-indolin]-2'-one 1'-((2,4-Dichloropyrimidin-5-yl)methyl)-6'-fluorospiro[cyclopropane-1,3'-indolin]-2'-one from Preparatory Example 4 (145 mg, 0.43 mmol, 1 eq.), isopentylamine (51 μl, 0.59 mmol, 1 eq.) and NaHCO$_3$ (86 mg, 1.02 mmol, 2.38 eq.) in EtOH (6 ml) were heated at reflux for 1 h and the mixture was stirred overnight at rt. EtOH was removed under reduced pressure and water (20 ml) was added to the residue. The precipitate was collected by filtration affording the title compound (166 mg, 99%) as an off-white solid.
$^1$H NMR (400 MHz, DMSO) δ 8.11 (s, 1H), 7.06 (s, 1H, NH), 6.82-6.74 (m, 3H), 4.72 (s, 2H), 3.47-3.42 (m, 2H), 1.81-1.78 (m, 2H), 1.67-1.59 (m, 3H), 1.48 (q, J=7.2 Hz, 2H), 0.95 (d, J=6.4 Hz, 6H). MS CI 390.1 [M+H]$^+$ Compounds prepared in a manner analogous to Preparatory Example 5 are shown in the table below:

| Prep. Ex. | Structure | Name | Data |
|---|---|---|---|
| 6 | (structure) | 1'-((2-Chloro-4-(((1r,4r)-4-hydroxycyclohexyl)amino)pyrimidin-5-yl)methyl)-6'-fluorospiro[cyclopropane-1,3'-indolin]-2'-one | $^1$H NMR (400 MHz, DMSO) δ 8.29 (s, 1H), 7.24 (dd, J = 9.6, 2.4 Hz, 1H), 7.17 (d, J = 7.2 Hz, 1H, NH), 7.10 (dd, J = 8.0, 2.8 Hz, 1H), 6.88 (td, J = 10.0, 2.4 Hz, 1H), 4.81 (s, 2H), 4.59 (d, J = 4.4 Hz 1H), 3.43 (s, 1H), 1.87-1.85 (m, 4H), 1.76-1.73 (m, 2H), 1.61-1.58 (m, 2H), 1.25 (t, J = 9.6 Hz, 4H); MS CI 418.0 [M + H]$^+$. |

-continued

| Prep. Ex. | Structure | Name | Data |
|---|---|---|---|
| 8 | 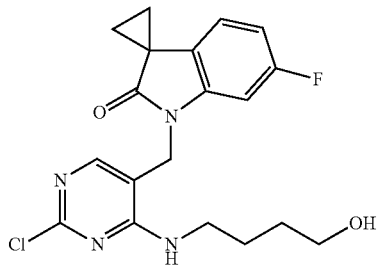 [SMILES: O=C1N(Cc2cnc(Cl)nc2NCCCCO)c2cc(F)ccc2C12CC2] | 1'-((2-Chloro-4-((4-hydroxybutyl)amino)pyrimidin-5-yl)methyl)-6'-fluorospiro[cyclopropane-1,3'-indolin]-2'-one | $^1$H NMR (400 MHz, CDCl$_3$) δ 8.14 (s, 1H), 7.41 (t, J = 5.2 Hz, 1H, NH), 7.21 (dd, J = 9.6, 2.4 Hz, 1H), 7.10 (dd, J = 8.4, 2.8 Hz, 1H), 6.88 (td, J = 8.4, 2.8 Hz, 1H), 4.81 (s, 2H), 4.43 (s, 1H), 3.42 (t, J = 6.4 Hz, 2H), 3.38-3.34 (m, 2H), 1.75-1.72 (m, 2H), 1.63-1.60 (m, 2H), 1.59-1.54 (m, 2H), 1.49-1.43 (m, 2H); MS CI 392.1 [M + H]$^+$. |
| 9 | 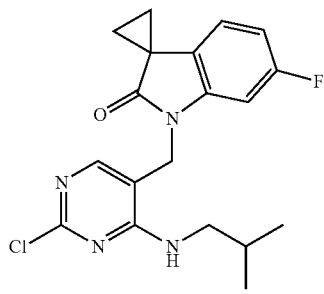 [SMILES: CC(C)CNc1nc(Cl)ncc1CN1C(=O)C2(CC2)c2ccc(F)cc21] | 1'-((2-Chloro-4-(isobutylamino)pyrimidin-5-yl)methyl)-6'-fluorospiro[cyclopropane-1,3'-indolin]-2'-one | $^1$H NMR (400 MHz, CDCl$_3$) δ 8.10 (s, 1H), 7.09 (s, 1H), 6.85-6.71 (m, 3H), 4.72 (s, 2H), 3.27 (dd, J = 6.9, 5.3 Hz, 2H), 1.97-1.84 (m, 1H), 1.82-1.76 (m, 2H), 1.62-1.56 (m, 2H), 0.94 (d, J = 6.7 Hz, 6H); MS CI 376.1 [M + H]$^+$. |
| 10 | 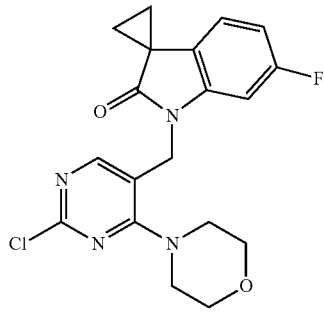 [SMILES: O=C1N(Cc2cnc(Cl)nc2N2CCOCC2)c2cc(F)ccc2C12CC2] | 1'-((2-Chloro-4-morpholinopyrimidin-5-yl)methyl)-6'-fluorospiro[cyclopropane-1,3'-indolin]-2'-one | $^1$H NMR (400 MHz, CDCl$_3$) δ 8.06 (s, 1H), 6.76-6.52 (m, 3H), 4.84 (s, 2H), 3.75-3.69 (m, 4H), 3.70-3.64 (m, 4H), 1.74-1.68 (m, 2H), 1.51-1.45 (m, 2H); MS CI 390.0 [M + H]$^+$. |
| 15 | 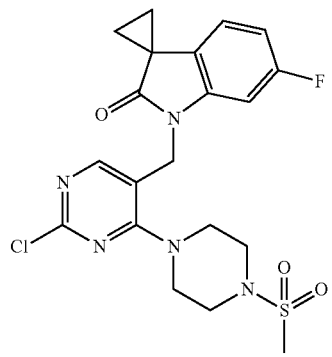 [SMILES: CS(=O)(=O)N1CCN(c2nc(Cl)ncc2CN2C(=O)C3(CC3)c3ccc(F)cc32)CC1] | 1'-{[2-Chloro-4-(4-methanesulfonyl-piperazin-1-yl)pyrimidin-5-yl]methyl}-6'-fluoro-1',2'-dihydrospiro[cyclopropane-1,3'-indole]-2'-one | $^1$H NMR (400 MHz, Chloroform-d) δ 8.00 (s, 1H), 6.79 (dd, J = 8.2, 5.2 Hz, 1H), 6.72 (td, J = 8.8, 8.3,2.2 Hz, 1H), 6.27 (dd, J = 8.7, 2.2 Hz, 1H), 4.83 (s, 2H), 3.69-3.62 (m, 4H), 3.44-3.36 (m, 4H), 2.84 (s, 3H), 1.83-1.78 (m, 2H), 1.61-1.54 (m, 2H). MS CI 466.1 [M + H]$^+$. |

-continued

| Prep. Ex. | Structure | Name | Data |
|---|---|---|---|
| 16 | 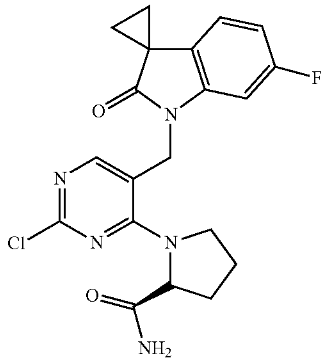 | 1-[2-Chloro-5-({6'-fluoro-2'-oxo-1',2'-dihydrospiro[cyclopropane-1,3'-indole]-1'-yl}methyl)pyrimidin-4-yl]pyrrolidine-2-carboxamide | $^1$H NMR (400 MHz, Chloroform-d) δ 7.83 (s, 1H), 6.82-6.68 (m, 2H), 6.62 (dd, J = 8.7, 2.1 Hz, 1H), 6.53 (s, 1H), 5.42 (s, 1H), 5.11-4.99 (m, 2H), 4.89-4.83 (m, 1H), 4.18-4.13 (m, 1H), 3.81-3.73 (m, 1H), 2.33-2.18 (m, 3H), 2.12-1.98 (m, 1H), 1.80-1.69 (m, 2H), 1.58-1.51 (m, 2H). MS CI 416.1 [M + H]$^+$. |
| 18 | 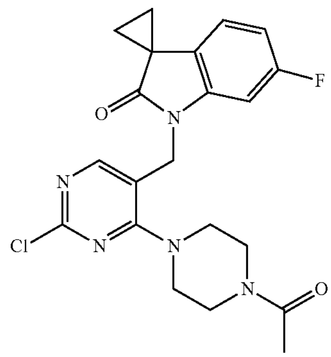 [SMILES: CC(=O)N1CCN(c2nc(Cl)ncc2CN2C(=O)C3(CC3)c3ccc(F)cc32)CC1] | 1'-{[4-(4-Acetylpiperazin-1-yl)-2-chloropyrimidin-5-yl]methyl}-6'-fluoro-1',2'-dihydrospiro[cyclopropane-1,3'-indole]-2'-one | $^1$H NMR (400 MHz, Chloroform-d) δ 8.00 (s, 1H), 6.81-6.68 (m, 2H), 6.28 (dd, J = 8.7, 2.2 Hz, 1H), 4.85 (s, 2H), 3.82-3.75 (m, 2H), 3.70-3.64 (m, 2H), 3.63-3.57 (m, 2H), 3.50-3.46 (m, 2H), 2.16 (s, 3H), 1.83-1.78 (m, 2H), 1.60-1.56 (m, 2H). MS CI 430.0 [M + H]$^+$. |
| 19 | 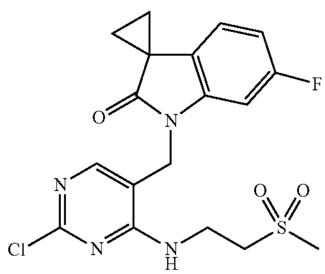 [SMILES: CS(=O)(=O)CCNc1nc(Cl)ncc1CN1C(=O)C2(CC2)c2ccc(F)cc21] | 1'-({2-Chloro-4-[(2-methanesulfonyl-ethyl)amino]pyrimidin-5-yl}methyl)-6-fluoro-1',2'-dihydrospiro[cyclopropane-1,3'-indole]-2'-one | $^1$H NMR (400 MHz, Chloroform-d) δ 8.17 (s, 1H), 7.72 (t, J = 5.7 Hz, 1H), 6.81-6.70 (m, 3H), 4.71 (s, 2H), 3.94 (td, J = 6.6, 5.6 Hz, 2H), 3.34 (t, J = 6.5 Hz, 2H), 2.96 (s, 3H), 1.91-1.81 (m, 2H), 1.62-1.57 (m, 2H). MS CI 425.0 [M + H]$^+$. |
| 20 | 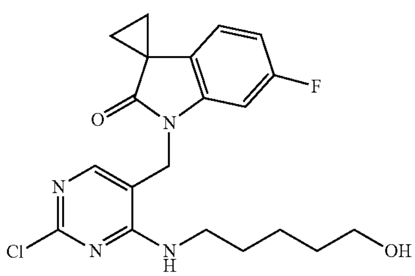 [SMILES: O=C1N(Cc2cnc(Cl)nc2NCCCCCO)c2cc(F)ccc2C12CC2] | 1'-({2-Chloro-4-[(5-hydroxypentyl)amino]pyrimidin-5-yl}methyl)-6'-fluoro-1',2'-dihydrospiro[cyclopropane-1,3'-indole]-2'-one | MS CI 405.0 [M + H]$^+$. R$_f$ = 0.79 (EtOAc) |
| 25 | 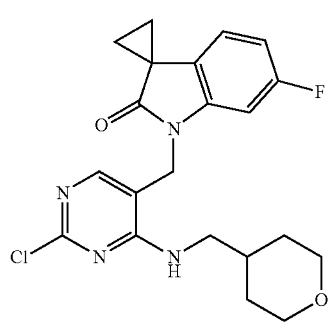 [SMILES: O=C1N(Cc2cnc(Cl)nc2NCC2CCOCC2)c2cc(F)ccc2C12CC2] | 1'-[(2-Chloro-4-{[(oxan-4-yl)methyl]amino}pyrimidin-5-yl)methyl]-6'-fluoro-1',2'-dihydrospiro[cyclopropane-1,3'-indole]-2'-one | $^1$H NMR (400 MHz, Chloroform-d) δ 8.12 (s, 1H), 7.19 (t, J = 4.8 Hz, 1H), 6.76 (ddd, J = 10.4, 6.6, 1.7 Hz, 3H), 4.71 (s, 2H), 4.01-3.93 (m, 2H), 3.45-3.29 (m, 4H), 1.92-1.79 (m, 1H), 1.79-1.74 (m, 2H), 1.64-1.57 (m, 4H), 1.40-1.27 (m, 2H). MS CI 418.1 [M + H]$^+$. |

-continued

| Prep. Ex. | Structure | Name | Data |
|---|---|---|---|
| 26 | 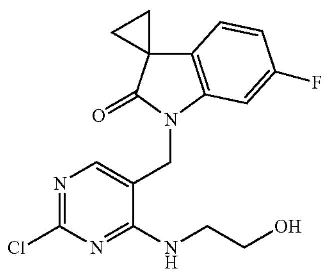 [SMILES: O=C1N(Cc2cnc(Cl)nc2NCCO)c2cc(F)ccc2C12CC2] | 1'-({2-Chloro-4-[(2-hydroxyethyl)amino]pyrimidin-5-yl}methyl)-6'-fluoro-1',2'-dihydrospiro[cyclopropane-1,3'-indole]-2'-one | $^1$H NMR (400 MHz, Chloroform-d) δ 8.13 (s, 1H), 7.49 (s, 1H), 6.86-6.68 (m, 3H), 4.74 (s, 2H), 3.80 (td, J = 6.0, 4.3 Hz, 2H), 3.67-3.53 (m, 2H), 2.73 (t, J = 6.1 Hz, 1H), 1.87-1.76 (m, 2H), 1.64-1.60 (m, 2H). MS CI 363.1 [M + H]$^+$. |
| 27 | 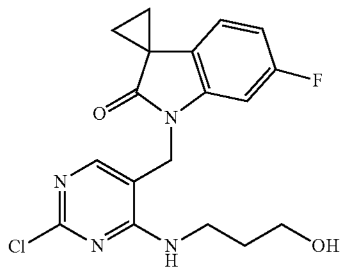 [SMILES: O=C1N(Cc2cnc(Cl)nc2NCCCO)c2cc(F)ccc2C12CC2] | 1'-({2-Chloro-4-[(3-hydroxypropyl)amino]pyrimidin-5-yl}methyl)-6'-fluoro-1',2'-dihydrospiro[cyclopropane-1,3'-indole]-2'-one | $^1$H NMR (400 MHz, Chloroform-d) δ 8.11 (s, 1H), 7.37 (t, J = 6.4 Hz, 1H), 6.81-6.73 (m, 3H), 4.72 (s, 2H), 3.65-3.54 (m,4H), 2.87 (t, J = 5.8 Hz, 1H), 1.85-1.74 (m, 4H), 1.67-1.57 (m, 2H). MS CI 377.2 [M + H]$^+$. |
| 28 | 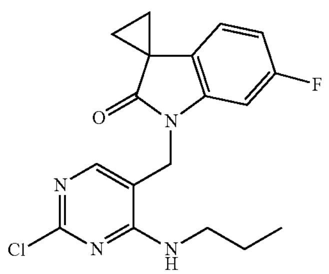 [SMILES: CCCNc1nc(Cl)ncc1CN1C(=O)C2(CC2)c2ccc(F)cc21] | 1'-{[2-Chloro-4-(propylamino)pyrimidin-5-yl]methyl}-6'-fluoro-1',2'-dihydrospiro[cyclopropane-1,3'-indole]-2'-one | $^1$H NMR (400 MHz, Chloroform-d) δ 8.10 (s, 1H), 7.10 (s, 1H), 6.90-6.70 (m, 3H), 4.71 (s, 2H), 3.48-3.33 (m, 2H), 1.85-1.74 (m, 2H), 1.66-1.57 (m, 4H), 0.94 (t, J = 7.4 Hz, 3H). MS CI 361.3 [M + H]$^+$. |
| 29 | 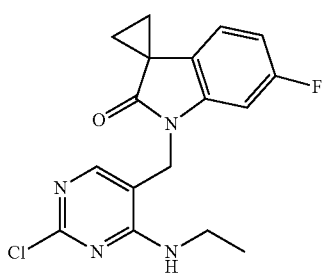 [SMILES: CCNc1nc(Cl)ncc1CN1C(=O)C2(CC2)c2ccc(F)cc21] | 1'-{[2-Chloro-4-(ethylamino)pyrimidin-5-yl]methyl}-6'-fluoro-1',2'-dihydrospiro[cyclopropane-1,3'-indole]-2'-one | $^1$H NMR (400 MHz, Chloroform-d) δ 8.09 (s, 1H), 7.11 (s, 1H), 6.84-6.63 (m, 3H), 4.71 (s, 2H), 3.46 (qd, J = 7.3, 4.9 Hz, 2H), 1.83-1.71 (m, 2H), 1.67-1.58 (m, 2H), 1.21 (t, J = 7.3 Hz, 3H). MS CI 347.3 [M + H]$^+$. |

Preparatory Example 7

1'-((2-Chloro-4-((2-morpholinoethyl)amino)pyrimidin-5-yl)methyl)-6'-fluorospiro[cyclopropane-1,3'-indolin]-2'-one A solution of 1'-((2,4-dichloropyrimidin-5-yl)methyl)-6'-fluorospiro[cyclopropane-1,3'-indolin]-2'-one from Preparatory Example 4 (0.20 g, 0.59 mmol, 1 eq.) in MeCN (6 ml) was treated with DIPEA (206 μl, 1.18 mmol, 2 eq.) and 4-(2-aminoethyl)morpholine (78 μl, 0.59 mmol, 1 eq.). The resulting solution was stirred at rt for 60 hours. MeCN was evaporated under reduced pressure, the residue dissolved into DCM (50 ml) and the organic layer extracted with HCl (0.5 M, 3×50 ml). The aqueous layers were basified to pH 7.8 (NaHCO$_3$). This solution was extracted with DCM (3×50 ml), the organic layer washed with brine (80 ml) and dried over Na$_2$SO$_4$. Evaporation of the solvent under reduced pressure provided the title compound (196 mg, 76%) as a white solid.

$^1$H NMR (400 MHz, CDCl$_3$) δ 8.12 (s, 1H), 7.19 (s, 1H, NH), 6.82-6.72 (m, 3H), 4.74 (s, 2H), 3.72 (t, J=4.4 Hz, 4H), 3.59 (q, J=6.4 Hz, 2H), 2.57 (t, J=6.4 Hz, 2H) 2.53 (t, J=4.4 Hz, 4H), 1.80-1.77 (m, 2H), 1.62-1.59 (m, 2H); MS CI 432.9 [M+H]$^+$.

Preparatory Example 11

1'-((2-Chloro-4-((tetrahydro-2H-pyran-4-yl)amino)pyrimidin-5-yl)methyl)-6'-fluorospiro[cyclopropane-1,3'-indolin]-2'-one 1'-((2,4-Dichloropyrimidin-5-yl)methyl)-6'-fluorospiro[cyclopropane-1,3'-indolin]-2'-one from Preparatory Example 4 (135 mg, 0.40 mmol, 1 eq.) in MeCN (4 ml) was treated with a solution of 4-aminotetrahydropyran (41 µl, 0.40 mmol, 1 eq.) and DIPEA (142 µl, 0.80 mmol, 2 eq.) in MeCN (2 ml). The mixture was stirred at rt for 60 hours and formation of a white precipitate was observed. The mixture was transferred to a microwave vial and heated in the microwave at 70° C. for 30 minutes. The precipitate was filtered off and dissolved in DCM. The solvent was removed under reduced pressure, the residue washed with a 19:1 heptane:EtOAc solution (×3) and dried to afford the title compound (78.1 mg, 49%) as an off white solid.

$^1$H NMR (400 MHz, CDCl$_3$) δ 8.08 (s, 1H), 7.16 (s, 1H, NH), 6.81-6.71 (m, 3H), 4.70 (s, 2H), 3.52 (td, J=7.0, 5.2 Hz, 2H), 3.44 (t, J=6.2 Hz, 2H), 3.32 (s, 3H), 1.90-1.83 (m, 2H), 1.82-1.77 (m, 2H), 1.60-1.57 (m, 2H); MS CI 404.1 [M+H]+.

Preparatory Example 12

1'-((2-Chloro-4-((3-methoxypropyl)amino)pyrimidin-5-yl)methyl)-6'-fluorospiro[cyclopropane-1,3'-indolin]-2'-one 1'-((2,4-Dichloropyrimidin-5-yl)methyl)-6'-fluorospiro[cyclopropane-1,3'-indolin]-2'-one from Preparatory Example 4 (135 mg, 0.40 mmol, 1 eq.) in MeCN (4 ml) was treated with DIPEA (142 µl, 0.80 mmol, 2 eq.) and 3-methoxypropylamine (43 µl, 0.40 mmol, 1 eq.). The resulting solution was stirred in a microwave at 70° C. for 20 minutes. MeCN was evaporated under reduced pressure, the residue dissolved in DCM (50 ml), the organic layer was washed with water (2×20 ml) and dried over MgSO$_4$, filtered and concentrated under reduced pressure. The residue was purified by flash column chromatography (15-75% heptane:EtOAc) providing the title compound (88 mg, 57%) as a white solid.

$^1$H NMR (400 MHz, CDCl$_3$) δ 8.08 (s, 1H), 7.16 (s, 1H, NH), 6.81-6.72 (m, 3H), 4.70 (s, 2H), 3.53 (td, J=7.0, 5.2 Hz, 2H), 3.44 (t, J=6.2 Hz, 2H), 3.32 (s, 3H), 1.91-1.83 (m, 2H), 1.81-1.77 (m, 2H), 1.61-1.58 (m, 2H); MS CI 390.8 [M+H]$^+$.

Preparatory Example 13

1'-((4-(3-Aminopyrrolidin-1-yl)-2-chloropyrimidin-5-yl)methyl)-6'-fluorospiro[cyclopropane-1,3'-indolin]-2'-one A mixture of 1'-((2,4-dichloropyrimidin-5-yl)methyl)-6'-fluorospiro[cyclopropane-1,3'-indolin]-2'-one from Preparatory Example 4 (135 mg, 0.40 mmol, 1 eq.), 3-aminopyrrolidine dihydrochloride (64.0 mg, 0.40 mmol, 1 eq.), NaHCO$_3$ (135 mg, 1.6 mmol, 4 eq.) and isopropanol (10 ml) was heated to reflux for 2 hours 30 minutes. The mixture was allowed to cool to rt, and isopropanol removed under reduced pressure. The residue was partitioned between water (20 ml) and DCM (20 ml). The organic layer was washed successively with water (20 ml) and brine (20 ml), dried over MgSO$_4$, filtered, concentrated under reduced pressure and purified by column chromatography (1:1 heptane:EtOAc to EtOAc) affording the title compound (52 mg, 34%) as an off white solid.

R$_f$=0.79 (9:1 DCM:MeOH); MS CI 388.9 [M+H]$^+$.

Preparatory Example 14

1'-((2-Chloro-4-(1,1-dioxidothiomorpholino)pyrimidin-5-yl)methyl)-6'-fluorospiro[cyclopropane-1,3'-indolin]-2'-one 1'-((2,4-Dichloropyrimidin-5-yl)methyl)-6'-fluoro spiro[cyclopropane-1,3'-indolin]-2'-one from Preparatory Example 4 (190 mg, 0.56 mmol, 1 eq.), thiomorpholine-S,S-dioxide (58 mg, 0.56 mmol, 1 eq.), NaHCO$_3$ (131 mg, 1.29 mmol, 2.32 eq.) and isopropanol (10 ml) were heated in a microwave at 100° C. for two 30 minute periods. Isopropanol was removed under reduced pressure. The residue was partitioned between DCM (15 ml) and water (15 ml). The organic layer was washed successively with water (15 ml) and brine (15 ml), dried over MgSO$_4$, filtered and concentrated under reduced pressure to afford 1'-((2-chloro-4-thiomorpholinopyrimidin-5-yl)methyl)-6'-fluorospiro[cyclopropane-1,3'-indolin]-2'one (265 mg) as an orange oil, which was used without further purification in the next step.

A solution of 1'-((2-chloro-4-thiomorpholinopyrimidin-5-yl)methyl)-6'-fluorospiro[cyclopropane-1,3'-indolin]-2'one (265 mg, 0.56 mmol) in DCM (15 ml) was cooled to 0° C. mCPBA (251 mg, 1.12 mmol, 2 eq.) was added in 5 portions over 5 minutes and the mixture allowed to warm to rt and stirred for a further 4 hours. The mixture was washed with NaHCO$_3$ (3×25 ml of a saturated solution), the aqueous washes extracted with DCM (3×25 ml), and the combined organics dried over MgSO$_4$, filtered and concentrated under reduced pressure. The residue was purified by column chromatography (9:1 heptane:EtOAc to 1:1 heptane:EtOAc) affording the title compound (66 mg, 20%) as a white solid.

$^1$H NMR (400 MHz, CDCl$_3$) δ 8.08 (s, 1H), 6.84-6.69 (m, 2H), 6.25 (dd, J=8.6, 2.2 Hz, 1H), 4.86 (s, 2H), 4.09-4.01 (m, 4H), 3.29-3.21 (m, 4H), 1.86-1.79 (m, 2H), 1.64-1.58 (m, 2H); MS CI 437.8 [M+H]$^+$.

Preparatory Example 17

1'-({2-Chloro-4-[(4-hydroxybutyl)sulfanyl]pyrimidin-5-yl}methyl)-6'-fluoro-1',2'-dihydrospiro[cyclopropane-1,3'-indole]-2'-one A mixture of 1'-((2,4-Dichloropyrimidin-5-yl)methyl)-6'-fluorospiro[cyclopropane-1,3'-indolin]-2'-one from Preparatory Example 4 (135 mg, 0.40 mmol, 1 eq.), mercaptobutanol (45 µl, 0.44 mmol, 1.1. eq.) and K$_2$CO$_3$ (110 mg, 0.80 mmol, 2 eq.) in DMF (8 ml) was heated at 80° C. for 2 hours. The mixture was cooled to rt and partitioned between EtOAc (10 ml) and water (10 ml). The aqueous layer was further extracted with EtOAc (2×10 ml) and the combined organics were washed successively with water (10 ml) and brine (10 ml), dried over MgSO$_4$, filtered and concentrated under reduced pressure. The residue was purified by column chromatography (1:4 to 4:1 EtOAc:heptane) to afford the title compound (61 mg, 37%) as an off-white solid.

R$_f$=0.78 (100:8:1 DCM:MeOH:NH$_3$); MS CI 409.1 [M+H]$^+$.

Preparatory Example 21

1'-[(2,4-dichloropyrimidin-5-yl)methyl]-6'-fluoro-1',2'-dihydrospiro[cyclobutane-1,3'-indole]-2'-one 2,4-Dichloro-5-(iodomethyl)pyrimidine from Preparatory Example 3 (510 mg, 1.77 mmol, 1 eq.), 6'-fluorospiro[cyclobutane-1,3'-indolin]-2'-one (338 mg, 1.77 mmol, 1 eq.) and K$_2$CO$_3$ (598 mg, 4.34 mmol, 2.45 eq.) in MeCN (12 ml) were heated to reflux for 3 hours. The mixture was allowed to cool to rt and MeCN was removed under reduced pressure. The residue was partitioned between DCM (20 ml) and water (20 ml). The organic layer was successively washed with water (10 ml) and brine (10 ml), dried over MgSO$_4$, filtered and concentrated under reduced pressure.

The residual solid was purified by column chromatography (14% EtOAc:heptane) to afford the title compound (338 mg, 82%) as a pale yellow solid.

$R_f$=0.67 (2:1 heptane:EtOAc); MS CI 381.1 [M–Cl+H]$^+$.

Preparatory Example 22

1'-{[2-(3-Aminopyrrolidin-1-yl)-4-[(4-hydroxycyclohexyl)amino]pyrimidin-5-yl]methyl}-6'-fluoro-1', 2'-dihydrospiro[cyclobutane-1,3'-indole]-2'-one 1'-[(2,4-Dichloropyrimidin-5-yl)methyl]-6'-fluoro-1',2'-dihydrospiro[cyclobutane-1,3'-indole]-2'-one from Preparatory Example 21 (145 mg, 0.43 mmol, 1 eq.), 4-amino cyclohexanol hydrochloride (45.4 mg, 0.30 mmol, 1 eq.) and NaHCO$_3$ (59.9 mg, 1.02 mmol, 2.38 eq.) in EtOH (4 ml) were heated at reflux for 5 h and the mixture was cooled to rt. EtOH was removed under reduced pressure and water (20 ml) was added to the residue. The precipitate was collected by filtration affording the title compound (68.5 mg, 43%) as a white solid.

$^1$H NMR (400 MHz, Chloroform-d) δ 8.05 (s, 1H), 7.45 (dd, J=8.2, 5.2 Hz, 1H), 7.01 (d, J=7.3 Hz, 1H), 6.82 (ddd, J=9.4, 8.3, 2.3 Hz, 1H), 6.61 (dd, J=8.7, 2.2 Hz, 1H), 4.58 (s, 2H), 4.07-3.93 (m, 1H), 3.78-3.65 (m, 1H), 2.68-2.55 (m, 2H), 2.47-2.19 (m, 4H), 2.08-1.98 (m, 4H), 1.57-1.29 (m, 6H). $R_f$=0.87 (100:8:1 DCM:MeOH:NH$_3$).

Preparatory Example 23

1'-{[2-Chloro-4-(5-hydroxypent-1-yn-1-yl)pyrimidin-5-yl]methyl}-6'-fluoro-1',2'-dihydrospiro[cyclopropane-1,3'-indole]-2'-one 1'-((2,4-Dichloropyrimidin-5-yl)methyl)-6'-fluorospiro[cyclopropane-1,3'-indolin]-2'-one from Preparatory Example 4 (1.01 g, 3.0 mmol, 1 eq.) and Pentyn-1-ol (0.42 ml, 4.5 mmol, 1.5 eq.) were added to a degassed solution of triethylamine (1.75 ml, 12.6 mmol, 4 eq.) in 1,4-Dioxane (10 ml). Copper iodide (28 mg, 4 mol %) and Bis(triphenylphosphine)palladium chloride (42 mg, 2 mol %) were added and the mixture was heated at 60° C. for 2 hours. The mixture was concentrated under reduced pressure and purified by column chromatography (1:1-6:4 EtOAc:heptane) to afford the title compound (1.03 g, 75%) as a yellow solid.

$^1$H NMR (400 MHz, Chloroform-d) δ 8.48 (s, 1H), 6.79 (dd, J=8.2, 5.2 Hz, 1H), 6.73 (ddd, J=9.4, 8.2, 2.2 Hz, 1H), 6.63 (dd, J=8.9, 2.2 Hz, 1H), 5.05 (s, 2H), 3.82 (td, J=6.0, 5.1 Hz, 2H), 2.72 (t, J=7.0 Hz, 2H), 1.94 (tt, J=7.0, 5.9 Hz, 2H), 1.82-1.78 (m, 2H), 1.59-1.55 (m, 2H). $R_f$=0.13 (1:1 heptanes:EtOAc).

Preparatory Example 24

1'-{[2-Chloro-4-(3-fluoropropoxy)pyrimidin-5-yl] methyl}-6'-fluoro-1',2'-dihydrospiro[cyclopropane-1, 3'-indole]-2'-one Sodium hydride (60% in mineral oil) (10.6 mg, 0.44 mmol, 1.1 eq.) was added to a solution of 3-fluoropropan-1-ol (30 μl, 0.4 mmol, 1 eq.) in DMF (3 ml) and the mixture was stirred at rt for 10 minutes. 1'-((2,4-Dichloropyrimidin-5-yl)methyl)-6'-fluorospiro[cyclopropane-1,3'-indolin]-2'-one from Preparatory Example 4 (135 mg, 0.4 mmol, 1 eq.) in DMF (1 ml) was added dropwise and the mixture was stirred at rt for 1 hour. Water (10 ml) was added and the mixture was extracted with EtOAc (2×10 ml). The organic layers were washed successively with water (2×10 ml) and brine (10 ml), dried over MgSO$_4$, filtered and evaporated under reduced pressure. The residue was purified by column chromatography (3:1 heptane:EtOAc) to afford the title compound (97 mg, 64%) as a pale yellow oil.

$^1$H NMR (400 MHz, Chloroform-d) δ 8.26 (s, 1H), 6.95-6.52 (m, 3H), 4.86 (s, 2H), 4.73-4.41 (m, 4H), 2.32-2.11 (m, 2H), 1.84-1.70 (m, 2H), 1.58-1.48 (m, 2H). MS CI 381.1 [M+H]$^+$.

Example 1

1'-((2-(3-Aminopyrrolidin-1-yl)-4-(isopentylamino) pyrimidin-5-yl)methyl)-6'-fluorospiro[cyclopropane-1,3'-indolin]-2'-one A mixture of 1'-((2-chloro-4-(isopentylamino)pyrimidin-5-yl)methyl)-6'-fluorospiro[cyclopropane-1,3'-indolin]-2'-one from Preparatory Example 5 (77.8 mg, 0.20 mmol, 1 eq.), 3-aminopyrrolidine dihydrochloride (32.0 mg, 0.20 mmol, 1 eq.), 2-dicyclohexylphosphino-2',4',6'-triisopropylbiphenyl (19.1 mg, 0.04 mmol, 20 mol %), cesium carbonate (260 mg, 0.80 mmol, 4 eq.) and Pd$_2$(dba)$_3$ (18.3 mg, 0.02 mmol, 10 mol %) in toluene (8 ml) was heated at 100° C. for 26 hours. Additional dicyclohexylphosphino-2',4',6'-triisopropylbiphenyl (10 mol %) and Pd$_2$(dba)$_3$ (5 mol %) were added and the reaction stirred for a further 19 hours at 100° C. The reaction mixture was allowed to cool to rt, concentrated under reduced pressure and purified by column chromatography (150:8:1 DCM:EtOH:NH$_3$) to afford the title compound (41.0 mg, 47%) as a light brown solid.

$^1$H NMR (400 MHz, CDCl$_3$) δ 7.98 (s, 1H), 6.82 (dd, J=8.9, 2.0 Hz, 1H), 6.77-6.68 (m, 2H), 6.42 (t, J=4.9 Hz, 1H, NH), 4.64 (s, 2H), 3.82-3.54 (m, 4H), 3.52 (td, J=7.2, 5.4 Hz, 2H), 3.28 (dd, J=11.1, 4.8 Hz, 2H), 2.21-2.10 (m, 5H), 1.78-1.70 (m, 3H), 1.68-1.55 (m, 2H), 1.55-1.51 (m, 2H), 1.47-1.42 (m, 2H), 1.26 (t, J=7.0 Hz, 1H), 0.92 (d, J=8.2 Hz, 6H); MS CI 439.9 [M+H]$^+$.

Example 2

1'-((2-(3-Aminopyrrolidin-1-yl)-4-(((r, 4r)-4-hydroxycyclohexyl)amino)pyrimidin-5-yl)methyl)-6'-fluorospiro[cyclopropane-1,3'-indolin]-2'-one A mixture of 1'-((2-chloro-4-(((1r,4r)-4-hydroxycyclohexyl)amino)pyrimidin-5-yl)methyl)-6'-fluorospiro[cyclopropane-1,3'-indolin]-2'-one from Preparatory Example 6 (140 mg, 0.335 mmol, 1 eq.), 3-aminopyrrolidine dihydrochloride (85.3 mg, 0.259 mmol, 1.6 eq.) and K$_2$CO$_3$ (184 mg, 1.33 mmol, 4 eq.) in DMF (7 ml) was heated at 100° C. for 16 hours. The mixture was cooled to rt and partitioned between EtOAc (10 ml) and water (10 ml). The aqueous layer was further extracted with EtOAc (2×10 ml) and the combined organics were washed successively with water (10 ml) and brine (10 ml), dried over MgSO$_4$, filtered and concentrated under reduced pressure. The residue was purified by column chromatography (DCM to 9:1 DCM:MeOH) to afford the title compound (51 mg, 33%) as an off-white solid.

$^1$H NMR (400 MHz, CDCl$_3$) δ 7.96 (s, 1H), 6.79 (dd, J=8.9, 1.9 Hz, 1H), 6.75-6.65 (m, 2H), 6.35 (d, J=6.9 Hz, 1H), 4.61 (s, 2H), 3.95-3.83 (m, 1H), 3.78-3.50 (m, 5H), 3.25 (dd, J=11.0, 4.6 Hz, 1H), 2.23-2.10 (m, 1H), 2.07-1.97 (m, 4H), 1.78-1.63 (m, 5H), 1.60-1.55 (m, 2H), 1.47-1.17 (m, 5H); MS CI 468.0 [M+H]$^+$.

Compounds prepared in a manner analogous to Example 2 are shown in the table below:

| Ex. | | Name | |
|---|---|---|---|
| 3 | 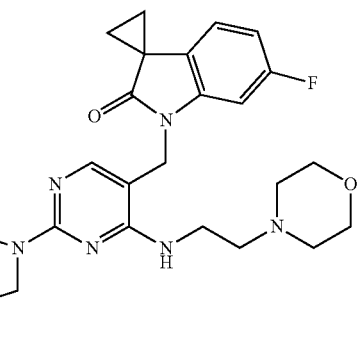 | 1'-((2-(3-Aminopyrrolidin-1-yl)-4-((2-morpholinoethyl)amino)pyrimidin-5-yl)methyl)-6'-fluorospiro[cyclopropane-1,3'-indolin]-2'-one | $^1$H NMR (400 MHz, CDCl$_3$) δ 7.97 (s, 1H), 6.79 (dd, J = 8.9, 2.0 Hz, 1H), 6.75-6.65 (m, 2H), 6.53 (t, J = 5.1 Hz, 1H, NH), 4.63 (s, 2H), 3.78-3.58 (m, 4H), 3.73-3.68 (m, 4H), 3.57-3.51 (td, J = 7.2, 5.4 Hz, 2H), 3.25 (dd, J = 11.1, 4.7 Hz, 1H), 2.54 (t, J = 7.0 Hz, 2H), 2.52-2.45 (m, 4H), 2.17-2.08 (m, 1H), 1.74-1.70 (m, 3H), 1.70-1.55 (m, 2H), 1.55-1.48 (m, 2H); MS CI 482.0 [M + H]$^+$. |
| 4 | 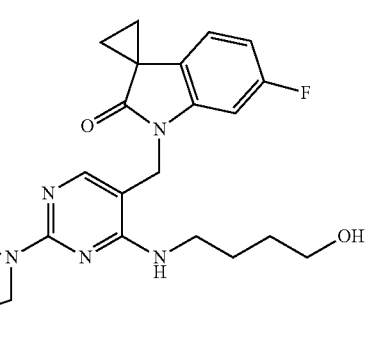 | 1'-((2-(3-Aminopyrrolidin-1-yl)-4-((4-hydroxybutyl)amino)pyrimidin-5-yl)methyl)-6'-fluorospiro[cyclopropane-1,3'-indolin]-2'-one | $^1$H NMR (400 MHz, CDCl$_3$) δ 7.98 (s, 1H), 6.81 (dd, J = 8.8, 2.0 Hz, 1H), 6.76-6.67 (m, 2H), 6.49 (s, 1H), 4.64 (s, 2H), 3.79-3.52 (m, 6H), 3.48-3.41 (m, 2H), 3.26 (dd, J = 11.1, 4.7 Hz, 1H), 2.19-2.09 (m, 1H), 1.78-1.73 (m, 2H), 1.71-1.57 (m, 8H), 1.56-1.51 (m, 2H); MS CI 442.0 [M + H]$^+$. |
| 5 | 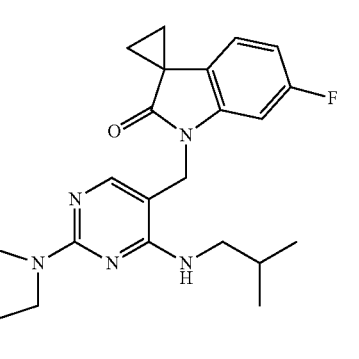 | 1'-((2-(3-Aminopyrrolidin-1-yl)-4-(isobutylamino)pyrimidin-5-yl)methyl)-6'-fluorospiro[cyclopropane-1,3'-indolin]-2'-one | $^1$H NMR (400 MHz, CDCl$_3$) δ 7.98 (s, 1H), 6.81 (dd, J = 8.9, 1.9 Hz, 1H), 6.76-6.65 (m, 2H), 6.50 (s, 1H, NH), 4.64 (s, 2H), 3.76 (dd, J = 11.2, 5.9 Hz, 1H), 3.73-3.52 (m, 3H), 3.29-3.20 (m, 1H), 3.22 (dd, J = 7.2, 5.4 Hz, 2H), 2.18-2.07 (m, 1H), 1.90 (dt, J = 13.4, 6.7 Hz, 1H), 1.72-1.67 (m, 2H), 1.65-1.52 (m, 3H), 1.54-1.49 (m, 2H), 0.89 (d, J = 6.7 Hz, 6H); MS CI 425.0 [M + H]$^+$. |
| 7 | 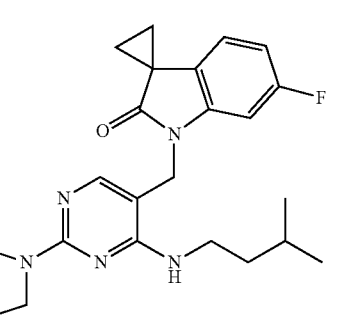 | 6'-Fluoro-1'-((4-(isopentylamino)-2-(pyrrolidin-1-yl)pyrimidin-5-yl)methyl)spiro[cyclopropane-1,3'-indolin]-2'-one | $^1$H NMR (400 MHz, CDCl$_3$) δ 7.97 (s, 1H), 6.82 (dd, J = 8.9, 2.0 Hz, 1H), 6.75-6.66 (m, 2H), 6.38 (t, J = 4.8 Hz, 1H, NH), 4.62 (s, 2H), 3.54-3.49 (m, 4H), 3.42 (td, J = 5.4, 7.2 Hz, 2H), 1.97-1.87 (m, 4H), 1.75-1.71 (m, 2H), 1.65-1.57 (m, 1H), 1.54-1.50 (m, 2H), 1.46-1.40 (m, 2H), 0.91 (d, J = 6.6 Hz, 6H). MS CI 424.0 [M + H]$^+$ |

| Ex. | | Name | |
|---|---|---|---|
| 8 | 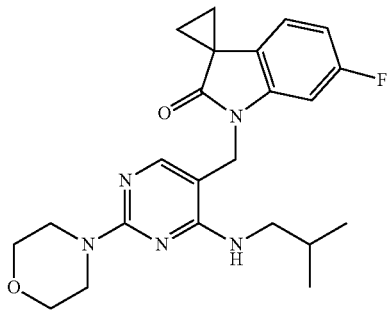 [SMILES: CC(C)CNc1nc(N2CCOCC2)ncc1CN1C(=O)C2(CC2)c2ccc(F)cc21] | 6'-Fluoro-1'-((4-(isobutylamino)-2-morpholinopyrimidin-5-yl)methyl)spiro[cyclopropane-1,3'-indolin]-2'-one | $^1$H NMR (400 MHz, CDCl$_3$) δ 7.98 (s, 1H), 6.81 (dd, J = 8.9, 2.0 Hz, 1H), 6.77-6.67 (m, 2H), 6.55 (t, J = 4.7 Hz, 1H, NH), 4.65 (s, 2H), 3.72 (s, 8H), 3.19 (dd, J = 7.2, 5.4 Hz, 2H), 1.95-1.82 (m, 1H), 1.77-1.72 (m, 2H), 1.55-1.51 (m, 2H), 0.91 (d, J = 6.7 Hz, 6H); MS CI 427.0 [M + H]$^+$. |
| 9 | 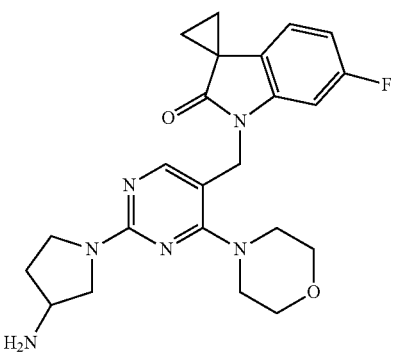 [SMILES: NC1CCN(c2ncc(CN3C(=O)C4(CC4)c4ccc(F)cc43)c(N3CCOCC3)n2)C1] | 1'-((2-(3-Aminopyrrolidin-1-yl)-4-morpholinopyrimidin-5-yl)methyl)-6'-fluorospiro[cyclopropane-1,3'-indolin]-2'-one | $^1$H NMR (400 MHz, CDCl$_3$) δ 7.87 (s, 1H), 6.75-6.62 (m, 2H), 6.44 (dd, J = 9.1, 2.2 Hz, 1H), 4.77 (s, 2H), 3.90-3.80 (m, 4H), 3.79-3.63 (m, 3H), 3.61-3.52 (m, 1H), 3.40-3.31 (m, 4H), 3.25 (dd, J = 10.9, 4.2 Hz, 1H), 2.20-2.10 (m, 1H), 1.82-1.71 (m, 2H), 1.59-1.43 (m, 4H); MS CI 438.9 [M + H]$^+$. |
| 13 | 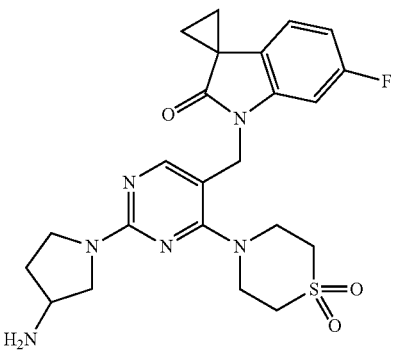 | 1'-((2-(3-Aminopyrrolidin-1-yl)-4-(1,1-dioxidothiomorpholino)pyrimidin-5-yl)methyl)-6'-fluorospiro[cyclopropane-1,3'-indolin]-2'-one | $^1$H NMR (400 MHz, CDCl$_3$) δ 7.93 (s, 1H), 6.77-6.63 (m, 2H), 6.34 (dd, J = 8.9, 2.2 Hz, 1H), 4.78 (s, 2H), 3.97-3.83 (m, 4H), 3.76-3.64 (m, 3H), 3.61-3.51 (m, 1H), 3.31-3.20 (m, 1H), 3.24-3.18 (m, 4H), 2.23-2.12 (m, 1H), 1.83-1.79 (m, 1H), 1.79-1.75 (m, 2H), 1.67-1.55 (s, 2H), 1.55-1.50 (m, 2H); MS CI 487.9 [M + H]$^+$. |
| 14 | 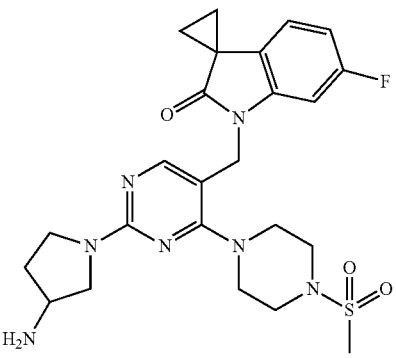 [SMILES: CS(=O)(=O)N1CCN(c2nc(N3CCC(N)C3)ncc2CN2C(=O)C3(CC3)c3ccc(F)cc32)CC1] | 1'-{[2-(3-Aminopyrrolidin-1-yl)-4-(4-methanesulfonylpiperazin-1-yl)pyrimidin-5-yl]methyl}-6'-fluoro-1',2'-dihydrospiro[cyclopropane-1,3'-indole]-2'-one | $^1$H NMR (400 MHz, CDCl$_3$) δ 7.90 (s, 1H), 6.73 (dd, J = 8.2, 5.2 Hz, 1H), 6.69-6.61 (m, 1H), 6.42 (dd, J = 9.0, 2.2 Hz, 1H), 4.77 (s, 2H), 3.74-3.63 (m, 3H), 3.57 (dd, J = 10.9, 5.5 Hz, 1H), 3.52-3.44 (m, 4H), 3.43-3.34 (m, 4H), 3.25 (dd, J = 10.8, 3.9 Hz, 1H), 2.83 (s, 3H), 2.21-2.10 (m, 1H), 1.82-1.68 (m, 3H), 1.64-1.53 (m, 2H), 1.54-1.48 (m, 2H). MS CI 516.0 [M + H]$^+$. |

| Ex. | | Name | |
|---|---|---|---|
| 15 | 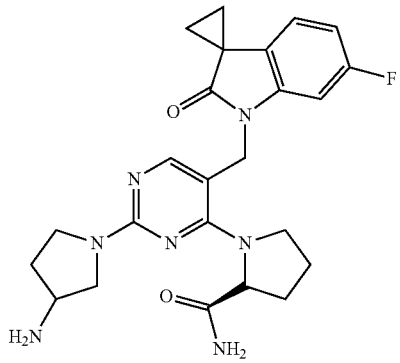 | 1-[2-(3-Aminopyrrolidin-1-yl)-5-({6'-fluoro-2'-oxo-1',2'-dihydrospiro[cyclopropane-1,3'-indole]-1'-yl}methyl)pyrimidin-4-yl]pyrrolidine-2-carboxamide | $^1$H NMR (400 MHz, Chloroform-d) δ 7.90 (s, 1H), 6.88 (s, 1H), 6.79-6.64 (m, 3H), 5.18 (s, 1H), 5.05 (d, J = 15.6 Hz, 1H), 4.86 (t, J = 7.6 Hz, 1H), 4.73 (d, J = 15.6 Hz, 1H), 4.19-4.10 (m, 1H), 3.75-3.45 (m, 5H), 3.23 (dd, J = 11.0, 3.7 Hz, 1H), 2.42-2.31 (m, 1H), 2.16 (s, 3H), 2.14-2.02 (m, 3H), 1.98-1.88 (m, 1H), 1.68 (dd, J = 9.8, 4.4 Hz, 1H), 1.61 (dd, J = 9.8, 4.4 Hz, 1H), 1.51-1.45 (m, 2H). MS CI 466.0 [M + H]$^+$. |
| 16 | 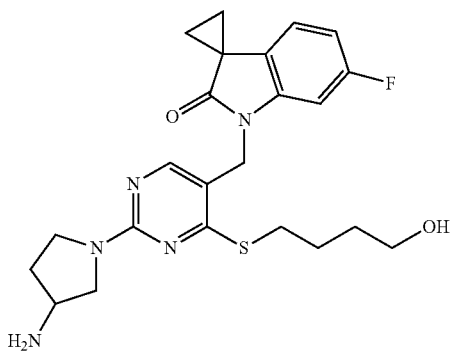 [SMILES: NC1CCN(c2ncc(CN3C(=O)C4(CC4)c4ccc(F)cc43)c(SCCCCO)n2)C1] | 1'-{[2-(3-Aminopyrrolidin-1-yl)-4-[(4-hydroxybutyl)sulfanyl]pyrimidin-5-yl]methyl}-6'-fluoro-1',2'-dihydrospiro[cyclopropane-1,3'-indole]-2'-one | $^1$H NMR (400 MHz, Chloroform-d) δ 7.83 (s, 1H), 6.83-6.56 (m, 3H), 4.78 (s, 2H), 3.79-3.64 (m, 2H), 3.69 (t, J = 6.4 Hz, 3H), 3.64-3.55 (m, 1H), 3.36-3.21 (m, 1H), 3.27 (t, J = 7.3 Hz, 2H), 2.23-2.09 (m, 1H), 1.90-1.79 (m, 2H), 1.80-1.67 (m, 5H), 1.68-1.53 (m, 3H), 1.54-1.45 (m, 2H). MS CI 458.0 [M + H]$^+$. |
| 17 | 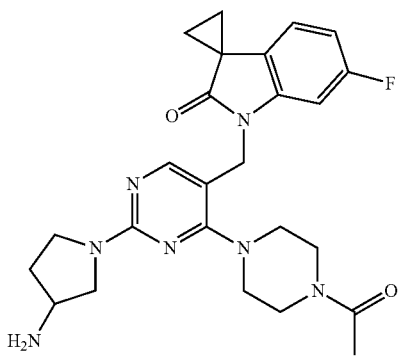 [SMILES: CC(=O)N1CCN(c2nc(N3CCC(N)C3)ncc2CN2C(=O)C3(CC3)c3ccc(F)cc32)CC1] | 1'-{[4-(4-Acetylpiperazin-1-yl)-2-(3-aminopyrrolidin-1-yl)pyrimidin-5-yl]methyl}-6'-fluoro-1',2'-dihydrospiro[cyclopropane-1,3'-indole]-2'-one | $^1$H NMR (400 MHz, Chloroform-d) δ 7.89 (s, 1H), 6.72 (dd, J = 8.2, 5.2 Hz, 1H), 6.68-6.62 (m, 1H), 6.43 (dd, J = 9.1, 2.2 Hz, 1H), 4.78 (s, 2H), 3.79-3.60 (m, 7H), 3.59-3.51 (m, 1H), 3.42-3.30 (m, 4H), 3.26 (dd, J = 10.8, 4.0 Hz, 1H), 2.20-2.11 (m, 1H), 2.15 (s, 3H), 1.82-1.72 (m, 3H), 1.71-1.64 (m, 2H), 1.53-1.49 (m, 2H). MS CI 480.2 [M + H]$^+$. |
| 18 | 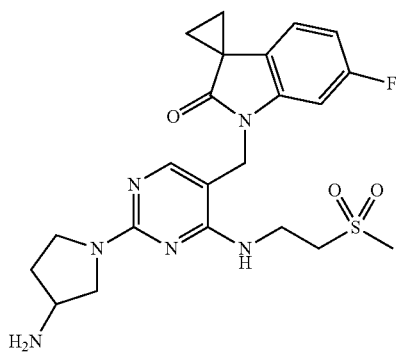 | 1'-{[2-(3-Aminopyrrolidin-1-yl)-4-[(2-methanesulfonylethyl)amino]pyrimidin-5-yl]methyl}-6'-fluoro-1',2'-dihydrospiro[cyclopropane-1,3'-indole]-2'-one | $^1$H NMR (400 MHz, Chloroform-d) δ 8.02 (s, 1H), 6.97 (t, J = 5.5 Hz, 1H), 6.82-6.66 (m, 3H), 4.62 (s, 2H), 3.90 (q, J = 6.3 Hz, 2H), 3.78-3.62 (m, 3H), 3.61-3.53 (m, 1H), 3.38 (t, J = 6.7 Hz, 2H), 3.26 (dd, J = 10.9, 4.2 Hz, 1H), 2.83 (s, 3H), 2.21-2.08 (m, 1H), 1.81-1.76 (m, 2H), 1.77-1.68 (m, 1H), 1.70-1.54 (m, 2H), 1.57-1.52 (m, 2H). MS CI 455.1 [M + H]$^+$. |

| Ex. | Name | | |
|---|---|---|---|
| 19 | 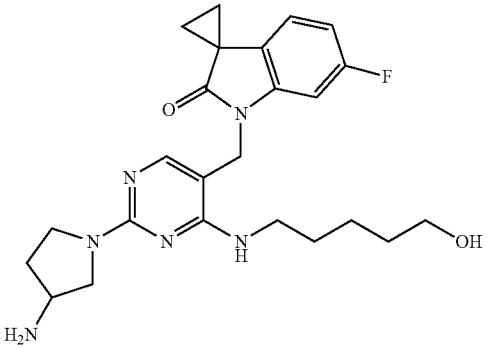 [SMILES: NC1CCN(c2ncc(CN3C(=O)C4(CC4)c4ccc(F)cc43)c(NCCCCCO)n2)C1] | 1'-{[2-(3-Aminopyrrolidin-1-yl)-4-[(5-hydroxypentyl)amino]pyrimidin-5-yl]methyl}-6'-fluoro-1',2'-dihydrospiro[cyclopropane-1,3'-indole]-2'-one | $^1$H NMR (400 MHz, CDCl$_3$) δ 7.96 (s, 1H), 6.81 (dd, J = 8.9, 1.9 Hz, 1H), 6.75-6.65 (m, 2H), 6.45 (t, J = 4.9 Hz, 1H), 4.62 (s, 2H), 3.74 (dd, J = 11.2, 5.9 Hz, 1H), 3.71-3.60 (m, 4H), 3.55 (ddd, J = 11.2, 7.9, 6.1 Hz, 1H), 3.41 (dt, J = 6.2, 5.6 Hz, 2H), 3.27 (dd, J = 11.2, 4.7 Hz, 1H), 2.13 (td, J = 12.8, 6.4 Hz, 1H), 1.86-1.68 (m, 9H), 1.60 (dt, J = 11.4, 4.0 Hz, 4H), 1.53 (q, J = 4.3 Hz, 2H), 1.47-1.38 (m, 2H). R$_f$ 0.40 (9:1 CH$_2$Cl$_2$:MeOH). |

Example 6

1'-((2-(4-Aminomethyl)piperidin-1-yl)-4-(isobutylamino)pyrimidin-5-yl)methyl)-6'-fluorospiro[cyclopropane-1,3'-indolin]-2'-one A solution of 1'-((2-chloro-4-(isobutylamino)pyrimidin-5-yl)methyl)-6'-fluorospiro[cyclopropane-1,3'-indolin]-2'-one from Preparatory Example 9 (75 mg, 0.2 mmol) and 4-(aminomethyl)piperidine (17 μl, 0.2 mmol) in toluene (8 ml), was treated with cesium carbonate (130 mg, 2 eq.). Dicyclohexylphosphino-2',4',6'-triisopropylbiphenyl (GD2) (23.7 mg, 15 mol %) was added and the mixture heated at 100° C. for 26 hours. The mixture was allowed to cool, toluene removed under reduced pressure and purified by column chromatography (200:8:1 DCM:EtOH:NH$_3$) affording the title compound as an off white solid (21 mg, 23%).

$^1$H NMR (400 MHz, CDCl$_3$) δ 7.96 (s, 1H), 6.81 (dd, J=8.8, 2.0 Hz, 1H), 6.76-6.67 (m, 2H), 6.48 (d, J=5.0 Hz, 1H), 4.76-4.70 (m, 2H), 4.63 (s, 2H), 3.20 (dd, J=6.7, 5.4 Hz, 2H), 2.78 (td, J=13.1, 2.6 Hz, 2H), 2.58 (d, J=6.5 Hz, 2H), 1.93-1.83 (m, 1H), 1.80-1.75 (m, 1H), 1.77-1.73 (m, 2H), 1.61-1.45 (m, 8H), 1.19-1.07 (m, 2H), 0.91 (d, J=6.7 Hz, 6H); MS CI 453.0 [M+H]$^+$.

Example 10

1'-((2-(3-Aminopyrrolidin-1-yl)-4-((tetrahydro-2H-pyran-4-yl)amino)pyrimidin-5-yl)methyl)-6'-fluorospiro[cyclopropane-1,3'-indolin]-2'-one A mixture of 1'-((2-chloro-4-((tetrahydro-2H-pyran-4-yl)amino)pyrimidin-5-yl)methyl)-6'-fluorospiro[cyclopropane-1,3'-indolin]-2'-one from Preparatory Example 11 (68 mg, 0.17 mmol, 1 eq.), 3-aminopyrrolidine dihydrochloride (29.7 mg, 0.19 mmol, 1.1 eq.) and K$_2$CO$_3$ (70.5 mg, 0.51 mmol, 3 eq.) in DMF (4 ml) was heated at 140° C. for 15 minutes in a microwave, followed by 30 minutes at 150° C. Water (15 ml) was added and the mixture was extracted with EtOAc (3×10 ml), the organics were washed with water (3×15 ml), dried over MgSO$_4$, filtered and concentrated under reduced pressure. Purification by column chromatography (0 to 20% MeOH:DCM+1% NH$_3$) afforded the title compound (14.2 mg, 18%) as a yellow solid.

$^1$H NMR (400 MHz, CDCl$_3$) δ 8.00 (s, 1H), 6.85-6.68 (m, 3H), 6.59-6.48 (m, 1H), 4.65 (s, 2H), 4.20-4.07 (m, 1H), 3.99 (dt, J=11.6, 3.6 Hz, 2H), 3.82-3.59 (m, 3H), 3.52 (td, J=11.6, 2.4 Hz, 2H), 3.26 (dd, J=10.9, 4.4 Hz, 1H), 2.21-2.10 (m, 1H), 2.03-1.91 (m, 2H), 1.81-1.73 (m, 2H), 1.80-1.50 (m, 6H), 1.59-1.52 (m, 2H); MS CI 454.1 [M+H]$^+$.

Example 11

1'-((2-(3-Aminopyrrolidin-1-yl)-4-((3-methoxypropyl)amino)pyrimidin-5-yl)methyl)-6'-fluorospiro[cyclopropane-1,3'-indolin]-2'-one 1'-((2-Chloro-4-((3-methoxypropyl)amino)pyrimidin-5-yl)methyl)-6'-fluorospiro[cyclopropane-1,3'-indolin]-2'-one from Preparatory Example 12 (77.7 mg, 0.2 mmol, 1 eq.), 3-aminopyrrolidine dihydrochloride (35.0 mg, 0.22 mmol, 1.1 eq.), K$_2$CO$_3$ (82.9 mg, 0.6 mmol, 3 eq.) and DMF (4 ml) were heated in a microwave at 140° C. for 30 minutes followed by another 15 mins at 150° C. Water (15 ml) was added and the mixture was extracted EtOAc (3×10 ml), the combined organics were washed with water (3×15 ml), dried over MgSO$_4$, filtered and concentrated under reduced pressure. The residue was purified by column chromatography (1% NH$_3$ in DCM:MeOH) 100:0 to 90:10 affording the title compound (28.4 mg, 32%) as an orange solid.

$^1$H NMR (400 MHz, CDCl$_3$) δ 7.96 (s, 1H), 6.80 (dd, J=8.9, 2.0 Hz, 1H), 6.76-6.66 (m, 2H), 6.49 (t, J=5.3 Hz, 1H), 4.62 (s, 2H), 3.84-3.51 (m, 4H), 3.47 (td, J=6.8, 5.4 Hz, 2H), 3.41 (t, J=6.4 Hz, 2H), 3.31 (s, 3H), 3.25 (dd, J=11.1, 4.8 Hz, 1H), 2.17-2.08 (m, 1H), 1.89-1.81 (m, 2H), 1.77-1.72 (m, 2H), 1.75-1.68 (m, 1H), 1.58 (s, 2H), 1.55-1.50 (m, 2H); MS CI 440.9 [M+H]$^+$.

Example 12

1'-((4-(3-Aminopyrrolidin-1-yl)-2-((4-hydroxybutyl)amino)pyrimidin-5-yl)methyl)-6'-fluorospiro[cyclopropane-1,3'-indolin]-2'-one 1'-((4-(3-Aminopyrrolidin-1-yl)-2-chloropyrimidin-5-yl)methyl)-6'-fluorospiro[cyclopropane-1,3'-indolin]-2'-one from Preparatory Example 13 (48 mg, 0.126 mmol, 1 eq.), 4-amino-1-butanol (19 μl, 0.201 mmol, 1.6 eq.), K$_2$CO$_3$ (17.4 mg, 0.126 mmol, 1 eq.) and DMF (4 ml) were heated at 100° C. for 3 hours, a further (13 μl, 0.126 mmol, 1 eq.) of 4-amino-1-butanol was added and the mixture heated for a further 5 hours. K$_2$CO$_3$ (34.8 mg, 0.252 mmol, 2 eq) was added and the mixture heated for a further 8 hours. Water (10 ml) and EtOAc (10 ml) were added. The aqueous layer was extracted with EtOAc (2×10 ml) and the combined organics were washed successively with water (2×10 ml) and brine (10 ml), dried over MgSO₄, filtered and concentrated under reduced pressure. The residue was purified by column chromatography (0-10% MeOH/DCM) affording the title compound (19.1 mg, 34%) as a white solid.

$^1$H NMR (400 MHz, CDCl$_3$) δ 7.51 (s, 1H), 6.80-6.60 (m, 2H), 6.49 (dd, J=9.0, 2.2 Hz, 1H), 4.95 (s, 2H), 4.93 (t, J=6.0 Hz, 1H), 3.92-3.81 (m, 2H), 3.77-3.69 (m, 1H), 3.69-3.62 (m, 3H), 3.45-3.33 (m, 3H), 2.24-2.08 (m, 1H), 1.90-1.56 (m, 8H), 1.79-1.74 (m, 2H), 1.54-1.49 (m, 2H); MS CI 442.0 [M+H]⁺.

Example 20

1'-{[2-(3-Aminopyrrolidin-1-yl)-4-[(4-hydroxycyclohexyl)amino]pyrimidin-5-yl]methyl}-6'-fluoro-1',2'-dihydrospiro[cyclobutane-1,3'-indole]-2'-one 1'-{[2-(3-Aminopyrrolidin-1-yl)-4-[(4-hydroxycyclohexyl)amino]pyrimidin-5-yl]methyl}-6'-fluoro-1',2'-dihydrospiro[cyclobutane-1,3'-indole]-2'-one from Preparatory Example 22 (57.5 mg, 0.133 mmol, 1 eq.), 3-aminopyrrolidine dihydrochloride (34.0 mg, 0.214 mmol, 1.6 eq.), K₂CO₃ (73.8 mg, 0.534 mmol, 4 eq.) and MeCN (6 ml) were heated at reflux for 21 hours. MeCN was evaporated under reduced pressure. Water (10 ml) and DCM (10 ml) were added. The organic layer was washed with water (2×10 ml). The aqueous layer was extracted with DCM (10 ml) and the combined organics were washed with brine (10 ml), dried over MgSO₄, filtered and concentrated under reduced pressure. The residue was purified by column chromatography (1-10% MeOH/DCM) affording the title compound (40.3 mg, 63%) as a white solid.

$^1$H NMR (400 MHz, CDCl$_3$) δ 7.92 (s, 1H), 7.40 (dd, J=8.2, 5.3 Hz, 1H), 6.75 (td, J=9.5, 2.2 Hz, 1H), 6.66 (dd, J=8.9, 2.2 Hz, 1H), 6.33 (d, J=6.9 Hz, 1H), 4.51 (s, 2H), 3.99-3.84 (m, 1H), 3.80-3.60 (m, 4H), 3.59-3.50 (m, 1H), 3.24 (dd, J=11.1, 4.6 Hz, 1H), 2.70-2.55 (m, 2H), 2.43-2.20 (m, 4H), 2.18-1.97 (m, 5H), 1.80-1.68 (m, 2H), 1.64 (d, J=31.0 Hz, 6H), 1.48-1.26 (m, 5H).

MS CI 481.2 [M+H]⁺.

Compounds prepared in a manner analogous to Example 20 are shown in the table below:

| Ex. | | Name | |
|---|---|---|---|
| 21 | | 1'-{[2-(3-Aminopyrrolidin-1-yl)-4-(5-hydroxypent-1-yn-1-yl)pyrimidin-5-yl]methyl}-6'-fluoro-1',2'-dihydrospiro[cyclopropane-1,3'-indole]-2'-one | $^1$H NMR (400 MHz, DMSO-d$_6$) δ 8.23 (s, 1H), 7.05 (dd, J = 8.2, 5.5 Hz, 1H), 6.92 (dd, J = 9.7, 2.3 Hz, 1H), 6.80 (ddd, J = 10.5, 8.2, 2.3 Hz, 1H), 4.87 (s, 2H), 4.55 (dt, J = 23.9, 5.1 Hz, 2H), 3.59-3.46 (m, 5H), 3.46-3.37 (m, 3H), 3.16-3.07 (m, 1H), 2.35-2.26 (m, 2H), 2.02-1.93 (m, 1H), 1.77-1.50 (m, 6H). MS CI 436.2 [M + H]⁺. |
| 22 | | 1'-{[2-(3-Aminopyrrolidin-1-yl)-4-(3-fluoropropoxy)pyrimidin-5-yl]methyl}-6'-fluoro-1',2'-dihydrospiro[cyclopropane-1,3'-indole]-2'-one | $^1$H NMR (400 MHz, Chloroform-d) δ 8.08 (s, 1H), 6.75-6.60 (m, 3H), 4.75 (s, 2H), 4.62 (t, J = 5.8 Hz, 1H), 4.50 (t, J = 6.1 Hz, 3H), 3.77-3.63 (m, 3H), 3.61-3.52 (m, 1H), 3.26 (dd, J = 11.1, 4.5 Hz, 1H), 2.24-2.08 (m, 3H), 1.81-1.74 (m, 1H), 1.74-1.70 (m, 2H), 1.68-1.55 (m, 2H), 1.50-1.45 (m, 2H). MS CI 430.2 [M + H]⁺. |
| 23 | | 1'-{[2-(3-Aminopyrrolidin-1-yl)-4-{[(oxan-4-yl)methyl]amino}pyrimidin-5-yl]methyl}-6'-fluoro-1',2'-dihydrospiro[cyclopropane-1,3'-indole]-2'-one | $^1$H NMR (400 MHz, Chloroform-d) δ 7.98 (s, 1H), 6.81 (dd, J = 8.9, 1.9 Hz, 1H), 6.76-6.67 (m, 2H), 6.55 (t, J = 5.3 Hz, 1H), 4.63 (s, 2H), 3.98-3.91 (m, 2H), 3.75 (dd, J = 11.1, 6.0 Hz, 1H), 3.71-3.50 (m, 3H), 3.39-3.29 (m, 4H), 3.25 (dd, J = 11.1, 4.7 Hz, 1H), 2.19-2.08 (m, 1H), 1.93-1.77 (m, 1H), 1.79-1.68 (m, 3H), 1.66-1.55 (m, 4H), 1.57-1.49 (m, 2H), 1.31 (qd, J = 12.0, 4.5 Hz, 2H). MS CI 467.2 [M + H]⁺. |

| Ex. | Structure | Name | 1H NMR |
|---|---|---|---|
| 26 | 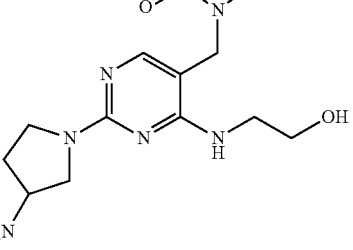 | 1'-{[2-(3-Aminopyrrolidin-1-yl)-4-[(2-hydroxyethyl)amino]pyrimidin-5-yl]methyl}-6'-fluoro-1',2'-dihydrospiro[cyclopropane-1,3'-indole]-2'-one | $^1$H NMR (400 MHz, Chloroform-d) δ 7.99 (s, 1H), 7.05 (t, J = 5.5 Hz, 1H), 6.89-6.66 (m, 3H), 4.64 (s, 2H), 3.78-3.49 (m, 8H), 3.24 (dd, J = 11.0, 4.6 Hz, 1H), 2.22-2.05 (m, 1H), 1.95-1.57 (m, 4H), 1.80-1.68 (m, 2H), 1.59-1.51 (m, 2H). MS CI 413.1 [M + H]$^+$. |
| 27 | 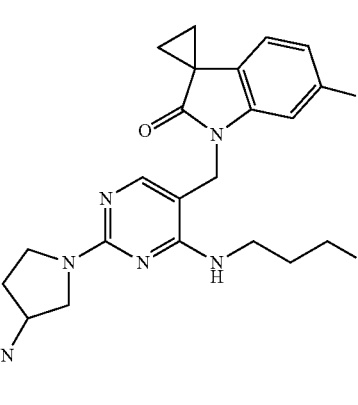 | 1'-{[2-(3-Aminopyrrolidin-1-yl)-4-[(3-hydroxypropyl)amino]pyrimidin-5-yl]methyl}-6'-fluoro-1',2'-dihydrospiro[cyclopropane-1,3'-indole]-2'-one | $^1$H NMR (400 MHz, Chloroform-d) δ 7.97 (s, 1H), 6.80 (dd, J = 8.8, 2.0 Hz, 1H), 6.77-6.66 (m, 3H), 4.63 (s, 2H), 3.78-3.42 (m, 8H), 3.25 (dd, J = 11.0, 4.7 Hz, 1H), 2.35-1.80 (m, 3H), 2.17-2.05 (m, 2H), 1.79-1.65 (m, 5H), 1.58-1.49 (m, 2H). MS CI 427.2 [M + H]$^+$. |
| 28 | 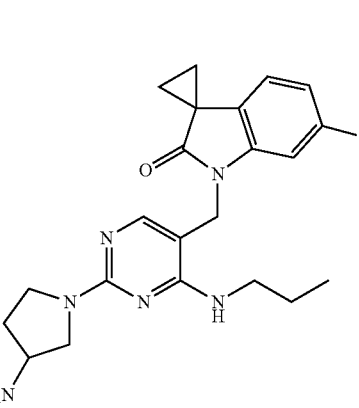 | 1'-{[2-(3-Aminopyrrolidin-1-yl)-4-(propylamino)pyrimidin-5-yl]methyl}-6'-fluoro-1',2'-dihydrospiro[cyclopropane-1,3'-indole]-2'-one | $^1$H NMR (400 MHz, Chloroform-d) δ 7.96 (s, 1H), 6.80 (dd, J = 9.0, 2.1 Hz, 1H), 6.76-6.65 (m, 2H), 6.44 (s, 1H), 4.63 (s, 2H), 3.82-3.47 (m, 4H), 3.35 (td, J = 7.0, 5.2 Hz, 2H), 3.26 (dd, J = 11.2, 4.8 Hz, 1H), 2.19-2.09 (m, 1H), 1.76-1.70 (m, 3H), 1.65-1.55 (m, 4H), 1.54-1.48 (m, 2H), 0.91 (t, J = 7.4 Hz, 3H). MS CI 411.4 [M + H]$^+$. |
| 29 | 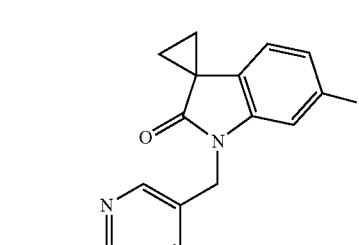 | 1'-{[2-(3-Aminopyrrolidin-1-yl)-4-(ethylamino)pyrimidin-5-yl]methyl}-6'-fluoro-1',2'-dihydrospiro[cyclopropane-1,3'-indole]-2'-one | $^1$H NMR (400 MHz, Chloroform-d) δ 7.96 (s, 1H), 6.80 (dd, J = 8.9, 2.1 Hz, 1H), 6.77-6.65 (m, 2H), 6.43 (s, 1H), 4.63 (s, 2H), 3.80-3.51 (m, 4H), 3.47-3.35 (m, 2H), 3.26 (dd, J = 11.1, 4.8 Hz, 1H), 2.13 (td, J = 12.3, 11.6, 5.7 Hz, 1H), 1.77-1.68 (m, 3H), 1.66-1.54 (m, 2H), 1.55-1.48 (m, 2H), 1.17 (t, J = 7.2 Hz, 3H). MS CI 397.4 [M + H]$^+$. |

Example 24

1'-{[2-(4-Aminopiperidin-1-yl)-4-[(4-hydroxybutyl) amino]pyrimidin-5-yl]methyl}-6'-fluoro-1',2'-dihydrospiro[cyclopropane-1,3'-indole]-2'-one 1'-((2-Chloro-4-((4-hydroxybutyl)amino)pyrimidin-5-yl) methyl)-6'-fluorospiro[cyclopropane-1,3'-indolin]-2'-one from Preparatory Example 8 (58.6 mg, 0.15 mmol, 1 eq.), 4-aminopiperidine (25 μl, 0.24 mmol, 1.6 eq.), $K_2CO_3$ (82.9 mg, 0.60 mmol, 4 eq.) and MeCN (5 ml) were heated at reflux for 76 hours. MeCN was evaporated under reduced pressure. Water (10 ml) and DCM (10 ml) were added. The organic layer was washed with water (2×10 ml). The aqueous layer was extracted with DCM (10 ml) and the combined organics were washed with brine (10 ml), dried over $MgSO_4$, filtered and concentrated under reduced pressure. The residue was purified by column chromatography (1-5% MeOH/DCM) affording the title compound (38.2 mg, 56%) as a white solid.

$^1$H NMR (400 MHz, Chloroform-d) δ 7.94 (s, 1H), 6.80 (dd, J=8.8, 2.0 Hz, 1H), 6.76-6.66 (m, 2H), 6.47 (t, J=5.1 Hz, 1H), 4.64 (s, 1H), 4.61 (s, 1H), 4.61 (s, 1H), 3.64 (t, J=6.0 Hz, 2H), 3.40 (td, J=6.3, 4.8 Hz, 2H), 2.91-2.81 (m, 3H), 1.87-1.78 (m, 4H), 1.76-1.72 (m, 3H), 1.70-1.57 (m, 5H), 1.55-1.50 (m, 2H), 1.24 (qd, J=12.5, 4.2 Hz, 2H). MS CI 455.1 [M+H]$^+$.

Example 25

1'-({2-[(2-Aminoethyl)amino]-4-[(4-hydroxybutyl) amino]pyrimidin-5-yl}methyl)-6'-fluoro-1',2'-dihydrospiro[cyclopropane-1,3'-indole]-2'-one 1'-((2-Chloro-4-((4-hydroxybutyl)amino)pyrimidin-5-yl) methyl)-6'-fluorospiro[cyclopropane-1,3'-indolin]-2'-one from Preparatory Example 8 (58.6 mg, 0.15 mmol, 1 eq.), ethylene diamine (16 μl, 2.4 mmol, 1.6 eq.), $K_2CO_3$ (20.7 mg, 0.15 mmol, 1 eq.) and MeCN (5 ml) were heated at reflux for 4 hours. Ethylene diamine (84 μl, 12.6 mmol, 8.4 eq.) was added and the mixture was heated at reflux for a further 72 hours. MeCN was evaporated under reduced pressure. Water (10 ml) and DCM (10 ml) were added. The organic layer was washed with water (2×10 ml). The aqueous layer was extracted with DCM (10 ml) and the combined organics were washed with brine (10 ml), dried over $MgSO_4$, filtered and concentrated under reduced pressure. The residue was purified by column chromatography (10% MeOH/DCM) affording the title compound (18.9 mg, 30%) as a colourless oil.

$^1$H NMR (400 MHz, Chloroform-d) δ 7.92 (s, 1H), 6.81 (dd, J=8.9, 2.1 Hz, 1H), 6.79-6.70 (m, 2H), 6.66 (t, J=5.4 Hz, 1H), 5.25 (s, 1H), 4.63 (s, 2H), 3.68 (t, J=6.0 Hz, 2H), 3.43 (dt, J=12.6, 6.4 Hz, 4H), 2.88 (t, J=6.0 Hz, 2H), 2.29-2.08 (m, 3H) 1.80-1.75 (m, 2H), 1.73-1.59 (m, 4H), 1.58-1.54 (m, 2H). MS CI 415.1 [M+H]$^+$.

Example 30: Biological Testing

Efficacy In Vitro

Compounds were subjected to RSV fusion assays and plaque reduction assays according to the following protocols.

RSV Fusion Assay

HEK 293T/17 cells were cultured in T75 culture flasks in Dulbecco's medium (DMEM) containing 10% FBS and 1× Penicillin-Streptomycin (Pen/Strep) and warmed to 37° C. prior to use. The cells were passaged by first washing briefly with 3 ml phosphate buffered saline (PBS) followed by a 4 min incubation with 3 TrypLE at 37° C. 7 ml media was then added to the flask and the cells dispersed via pipetting (×3) against the bottom of the flask. Two further T75 flasks were each seeded with 2×10$^6$ cells in 15 ml fresh media.

Cells were seeded on the T75 plates at the same density as on the 6-well plates the area of a T75 flask and one 1.75 cm radius well from a 6-well plate were compared. 7.79×2 ml of 3×10$^5$ cells ml$^{-1}$ was used to seed a single T75 flask.

HEK cells were removed from a T75 flask as described above. The cells were counted and diluted to 3×10$^5$ cells/ml in fresh media. Two T75 flasks were each seeded with 15.58 ml diluted cells.

The plasmid DNA (for pFR-Luc and pcDNA3.1_Gal4/ NFκB) to be transfected into the HEK cells was first prepared in serum free media (DMEM+Pen/Strep) containing the transfection reagent Fugene 6 (Promega). Transfections were set up as follows (Luc=pFR_Luc, Gal4=pcDNA3.1+_Gal4/NFκB, A2_F=pcDNA3.1+_A2_F)
Transfections
1 Luc+A2_F_1
2 Gal4

Serum free media was placed in a 1.5 ml eppendorf tube then the fugene 6 was added into the media. The tube was vortexed for 1 s before being incubated at RT for 5 min. The plasmid DNA was then added to the tube, vortexed for 1 s, then incubated at RT for 15 min The transfection reagents were then added to the appropriate T75 flask by tipping the flask on end and adding the reagents directly to the media already in the flask. The flask was then tipped on its back so the media could be mixed thoroughly whilst not disturbing the cells before placing the flask the right way up and incubating overnight at 37° C. and 5% $CO_2$.

Compounds were diluted (in a polypropylene round-bottomed 96 well plate) 1:3 in a twelve point dilution curve to give top [final] of either 3.3 μM, 1 μM, 500 nM 200 nM or 100 nM. The Control compound was always run at a concentration of 100 nM.

The cells were then counted and diluted to 4×10$^5$ cells/ml in fresh media. 50 μl of transfection population 1 cells were added to all wells of the assay plates. 100 μl diluted compound (2 rows per compound), standard curve (one row) and controls (100 nM RV (100% inhibition, four wells), DMSO (0% inhibition, eight wells)) were added to the appropriate wells. 50 μl of the diluted (4×10$^5$ cells/ml) transfection population 2 cells when then added to all wells.

The plates were then incubated for 24 hr at 37° C. and 5% $CO_2$

Buffers were prepared for the luciferase assay (20 mM tricine, 10 mM $MgSO_4$, 1 mM EDTA, 10 mM DTT) and lysis (25 mM tris-phosphate, 8 mM $MgCl_2$, 1 mM DTT, 1% Triton X-100, 15% glycerol) and stored at −20° C. Luciferin substrate was prepared from 100 mM Tris-HCl, 15.76 g/L, Coenzyme A, 10.36 g/L, 23.5 mM luciferin, 7.48 g/L, 26.6 mM ATP and 14.66 g/L and stored at −80° C.

Luminescence was measured as described:

(a) Luciferase

Media was discarded into Virkon and the plates washed with 100 ul PBS per well. 20 ul/well of lysis buffer was added to each well and incubated shaking for 5 min at RT. Luciferin was added to LAAB at a dilution of 1:50 to give a working luciferin buffer. 100 μl working luciferin buffer was added to each well and luminescence was measured immediately.

(b) Resazurin

Media was discarded into Virkon and 100 ul SFM+20 ul CellTitre-Blue solution was added to each well. The plates were incubated 37° C., 5% $CO_2$ for 2 hrs. Resorufin fluorescence was measured at 590 nm.

Plaque Reduction Assay 1:

Vero cells were seeded in 96-well plates in a volume of 100 μL of Optimem supplemented with 3% FCS at a concentration of $4 \times 10^4$ cells per well. After an overnight incubation at 37° C. in a humidified 5% $CO_2$ atmosphere, the monolayer of cells should be approximately 90% confluent. Antiviral compounds were titrated in pre-warmed Serum Free (SF) Optimem in a U-bottom 96 well plate. For compounds in a DMSO solution, titration in 100% DMSO was performed first and each concentration added individually to a 2× final concentration at 4% DMSO in SF media before mixing with virus (2% final DMSO with virus). Media was then removed from cells and replaced with PBS (100 μl/well).

RSV stock was thawed and diluted in SF Optimem media to 4000 PFU/mLl. An equal volume of virus was added to compounds on the titration plate. PBS was removed from cells which were then inoculated with the virus/compound solution (50 μL/well). Cells were incubated for 2 h in a 37° C.+5% $CO_2$ humidified incubator to allow infection. Inoculum was removed and media (Optimem+1% FCS) added to cells (100 μl/well). Cells were subsequently incubated for 48 h at 37° C.+5% $CO_2$ in a humidified incubator.

Immunostaining Procedure:

Media was removed from cells and the monolayer washed with PBS. Cells were fixed with ice cold 80% Acetone in PBS (100 μl/well) for 20 mins at −20° C. Fixative was removed and cells are dried for 30 mins with plates inverted. Blocking solution (5% skim milk powder in PBS-T) was added to cells (150 μL/well) and plates were incubated for 30 mins at room temperature. Blocking solution was removed and plates washed once with PBS-T. Primary antibody in blocking solution was added to plates (50 μl/well) and incubated for 1 h at 37° C. Plates were then washed 3 times with PBS-T. Secondary antibody in blocking solution was added to plates (50 L/well) and incubated for 1 h at 37° C. in the dark. Plates were washed as above and then dried for 10 mins. Plates were scanned on the Odyssey Imager (Li-Cor Biosciences) at a resolution of 42 M, medium quality and level 5 intensity in the 800 nM channel.

Data Analysis:

Images obtained were saved and plaque numbers counted with the aid of computer imaging software. $EC_{50}$ values for compounds were derived from dose response curves [three variable log(inhibitor) vs response] obtained using Graphpad Prism software.

TABLE 1

| Compound | RSV Plaque Reduction assays A2 (PRNT1) (n = 2) $IC_{50}$ (nM) |
|---|---|
| 1 | 619/316 |
| 2 | 18.9/4.63 |
| 4 | 5.48/9.3 |
| 5 | 165/215 |

Plaque Reduction Assay 2:

This RSV plaque reduction assay is an infectivity assay which allows quantification of the number of infectious units in a distinct foci of RSV infection. This is indicated by zones of viral antigen detected by specific antibody staining within a monolayer of otherwise healthy tissue culture cells. As each plaque originates from a single infectious virus particle an accurate calculation of the anti-viral effect can be obtained by counting plaques in the presence and absence of an anti-viral compound. HEp-2 cells (ATCC, CCL23) were passaged in flasks and seeded in 96-well plates in DMEM containing antibiotics and supplemented with 10% FBS. During inoculation and subsequent incubation, cells were cultured in DMEM containing 3% FBS. 100 plaque forming unit (PFU)/well of RSV (RSV A2 VR-1540) was mixed with ten serial dilutions of compound. Subsequently, 100 μL of the virus/compound mixtures was added to confluent HEp-2 cell monolayers. The cells and virus/compound mixtures were incubated at 35° C. in a humidified 5% $CO_2$ incubator for 1 day.

Cells were washed twice with PBS before adding 50% v/v EtOH/MeOH, and then stored at −20° C. On the day of the staining, fixative was first removed from the plates. Plates were washed 3× with PBS. A pre-titrated amount of the primary antibody was added in 60 μL PBS/2% milk powder, and plates incubated for 1 h at rt. The plates were washed 3× with PBS/0.05% Tween20 before addition of goat anti-mouse horse radish peroxidase in 60 μL PBS/2% milk powder, and incubated for 1 h at rt. Following three wash steps with PBS/0.05% Tween20, 60 μL ready-to-use True-Blue was added and plates were incubated at rt for 10-15 min before adding MilliQ water. Plates were washed once with water, incubated for 30-60 min and after removal of water, air-dried in the dark.

Plates were scanned and analyzed using the Immunospot S6 UV analyzer, which is equipped with BioSpot analysis software for counting immunostained plaques (virospots). Plaque counts were used to calculate % infection relative to the mean of the spot count (SC) in the virus control wells for RSV. IC50/IC90 values were calculated as 50% or 90% reduction in signal, respectively, by interpolation of inhibition curves fitted with a 4-parameter nonlinear regression with a variable slope in GraphPad 5.0 (Prism).

TABLE 3

| Compound | Fusion activity $IC_{50}$ μM | $PIC_{50}$ | Plaque activity $IC_{50}$ nM |
|---|---|---|---|
| 1 | 0.708 | 6.15 | |
| 2 | 0.237 | 6.63 | 58 |
| 3 | 4.18 | 5.38 | |
| 4 | 0.452 | 6.34 | 43 |
| 5 | 0.655 | 6.18 | 998 |
| 6 | 5.22 | 5.28 | |
| 7 | 1.99 | 5.70 | |
| 8 | 8.53 | 5.07 | |
| 9 | 3.66 | 5.44 | |
| 10 | 0.184 | 6.74 | 33 |
| 11 | 0.424 | 6.37 | |
| 12 | 4.78 | 5.32 | |
| 13 | 5.04 | 5.30 | 424 |
| 14 | 1.20 | 5.92 | |
| 15 | 2.50 | 4.60 | |
| 16 | 2.79 | 5.56 | |
| 17 | 5.46 | 5.26 | |
| 18 | 0.885 | 6.05 | |
| 19 | 0.362 | 6.44 | |
| 20 | 1.95 | 5.71 | 116 |
| 21 | 25 | 4.60 | |
| 22 | 0.951 | 6.02 | |
| 23 | 0.451 | 6.35 | |
| 24 | 0.695 | 6.16 | |

TABLE 3-continued

| Compound | Fusion activity IC$_{50}$ μM | PIC$_{50}$ | Plaque activity IC$_{50}$ nM |
|---|---|---|---|
| 25 | 0.212 | 6.67 | 49 |
| 26 | 2.50 | 4.60 | |
| 27 | 1.09 | 5.96 | 34 |
| 28 | 1.23 | 5.91 | 63 |
| 29 | 1.17 | 5.93 | 740 |

Example 31: In Vitro Pharmacokinetics

Compounds were subjected to the following assays to investigate liver microsomal stability, permeability, plasma protein binding and calculated partition/distribution coefficients.

Microsomal Incubation: Experimental Procedure

Pooled human liver microsomes (pooled male and female), pooled rat liver microsomes (male Sprague Dawley rats) and pooled dog liver microsomes (male Beagle dog) are purchased from a reputable commercial supplier and stored at −80° C. prior to use.

Microsomes (final protein concentration 0.5 mg/mL), 0.1 M phosphate buffer pH 7.4 and test compound (final substrate concentration 3 μM; final DMSO concentration 0.25%) are pre-incubated at 37° C. prior to the addition of NADPH (final concentration 1 mM) to initiate the reaction. The final incubation volume is 50 μL. A control incubation is included for each compound tested where 0.1 M phosphate buffer pH 7.4 is added instead of NADPH (minus NADPH). Two control compounds are included with each species. All incubations are performed singularly for each test compound.

Compounds are incubated for 0, 5, 15, 30 and 45 min. The control (minus NADPH) is incubated for 45 min only. The reactions are stopped by transferring 25 μL of incubate to 50 μL methanol at the appropriate time points. The termination plates are centrifuged at 2,500 rpm for 20 min at 4° C. to precipitate the protein. Following protein precipitation, the sample supernatants are combined in cassettes of up to 4 compounds, internal standard is added and samples analysed by LC-MS/MS. From a plot of ln peak area ratio (compound peak area/internal standard peak area) against time, the gradient of the line is determined. Subsequently, half-life and intrinsic clearance are calculated MDR I-MDCK Permeability: Experimental Procedure MDR1-MDCK cells obtained from the NIH (Rockville, Md., USA) are used between passage numbers 6-30. Cells are seeded onto Millipore Multiscreen Transwell plates at 3.4×105 cells/cm2. The cells are cultured in DMEM and media is changed on day 3. On day 4 the permeability study is performed. Cell culture and assay incubations are carried out at 37° C. in an atmosphere of 5% $CO_2$ with a relative humidity of 95%. On the day of the assay, the monolayers are prepared by rinsing both basolateral and apical surfaces twice with Hanks Balanced Salt Solution (HBSS) at the desired pH warmed to 37° C. Cells are then incubated with HBSS at the desired pH in both apical and basolateral compartments for 40 min to stabilise physiological parameters.

The dosing solutions are prepared by diluting test compound with assay buffer to give a final test compound concentration of 10 μM (final DMSO concentration of 1% v/v). The fluorescent integrity marker lucifer yellow is also included in the dosing solution. Analytical standards are prepared from test compound DMSO dilutions and transferred to buffer, maintaining a 1% v/v DMSO concentration.

For assessment of A-B permeability, HBSS is removed from the apical compartment and replaced with test compound dosing solution. The apical compartment insert is then placed into a companion plate containing fresh buffer (containing 1% v/v DMSO). For assessment of B-A permeability, HBSS is removed from the companion plate and replaced with test compound dosing solution. Fresh buffer (containing 1% v/v DMSO) is added to the apical compartment insert, which is then placed into the companion plate.

At 60 min the apical compartment inserts and the companion plates are separated and apical and basolateral samples diluted for analysis.

Test compound permeability is assessed in duplicate. Compounds of known permeability characteristics are run as controls on each assay plate.

Test and control compounds are quantified by LC-MS/MS cassette analysis using an 8-point calibration with appropriate dilution of the samples. The starting concentration (C0) is determined from the dosing solution and the experimental recovery calculated from C0 and both apical and basolateral compartment concentrations.

The integrity of the monolayer throughout the experiment is checked by monitoring lucifer yellow permeation using fluorimetric analysis. Lucifer yellow permeation is high if monolayers have been damaged.

Protein Binding Determination. Experimental Procedure

Solutions of test compound (5 μM, 0.5% final DMSO concentration) are prepared in buffer (pH 7.4) and 100% species-specific plasma. The experiment is performed using equilibrium dialysis with the two compartments separated by a semi-permeable membrane. The buffer solution is added to one side of the membrane and the plasma solution to the other side. After equilibration, samples are taken from both sides of the membrane. Standards are prepared in plasma and buffer and are incubated at 37° C. Test compound incubations are performed in duplicate. A control compound is included in each experiment.

The solutions for each batch of compounds are combined into two groups (protein-free and protein-containing), then cassette analysed by LC-MS/MS using two sets of calibration standards for protein-free (7 points) and protein-containing solutions (6 points).

Log D Determination: Experimental Procedure 0.1 M phosphate buffer pH 7.4 (saturated with octanol) is added to the vial containing 1 mg of solid test compound and the solution mixed and sonicated for approximately 15 min. The solution is transferred to tubes, centrifuged and the supernatant is drawn off the top, leaving any solid compound in the bottom. This supernatant is then syringe filtered through 0.2 μm filters to produce the initial solution.

Three vials are prepared containing different ratios of octanol and compound in phosphate buffer in order to cover a range of log D values. The vials are mixed to equilibrium, then centrifuged to ensure the two phases are fully separated before the octanol is removed and the buffer samples analysed.

The aqueous solutions from the corresponding vials are then combined in cassettes of four and analysed using generic LC-MS/MS conditions. The amount of compound in each vial is quantified against a 6 point standard curve which is produced by serially diluting the initial solution. The log D is then calculated from these concentrations.

Log P Determination

Log P values were calculated with software available from ChemAxon using the method described in Viswanadhan et al.; *J. Chem. Inf. Comput. Sci.* 1989; 29:163-172.

Results

For Example 2.

TABLE 4

| Pharmacokinetic Property | Value |
|---|---|
| Liver Microsomal Stability ($T_{1/2}$/mins; human/rat/dog) | 169 130 >240 |
| Permeability (Human Pgp transfected) MDCK $P_{app}$ (×10$^{-6}$ cm/s) A-B/B-A | 0.32/7.99 |
| PPB fraction unbound Rat/dog/human | |
| clogP/clogD | 1.93/ |

Example 32: In Vivo Pharmacokinetics

The pharmacokinetics of compounds were studied in vivo in MICE at doses of 1 mg/kg (IV) and 10 mg/kg (PO).

Methods

Sprague Dawley rats were treated with experimental compounds via intravenous and oral administration. Three animals for each route of administration were used with serial blood sampling at ten time points post dosing of compound.

An intravenous bolus was administered at a dose of 1 mg/kg and at a concentration of 1 mgml in 40:60 dimethyl acetamide/saline (0.9% w/v saline). Animals were weighed and used if between 200-250 g. Serial blood samples were collected at 0.02, 0.08, 0.25, 0.50, 1, 2, 4, 6, 8 and 24 hours post dosing. Animals were observed for any overt clinical signs or symptoms. Blood samples were delivered into an anticoagulant (sodium heparin) and centrifuged at 4° C. Plasma samples were subsequently stored frozen at less than −20° C. prior to analysis.

Following protein precipitation with acetonitrile, samples were analysed with tandem liquid chromatography/mass spectrometry using electrospray ionisation. A full matrix curve with internal standards was employed and PK parameters were calculated.

In a similar manner, oral administration was performed by gavage at doses of 5 or 10 mg/kg at a concentration of 5 mg/ml in 1% Methyl cellulose (Sigma M7140), 0.1% Tween 80 in water. Serial samples were taken as described above.

Results

TABLE 5

| Pharmacokinetic Property | Value |
|---|---|
| Volume of distribution (L/kg) | 8.1 |
| $C_{max}$ PO (ng/ml) | 52.4 |
| Bioavailability (%) | 7.6 |

Example 33: Aqueous Formulation

The compound of Example 1 is formulated as a solution in 30% w/v captisol (i.e. sulfobutylether-beta-cyclodextrin) at pH4 according to the following procedure.

A carrier of 30% w/v captisol (i.e. sulfobutylether-beta-cyclodextrin) is prepared by weighing the required amount of captisol into a suitable vessel, adding approximately 80% of the final volume of water and magnetically stirring until a solution is formed. The carrier is then made up to volume with water.

An aqueous solution of a compound of Example 1 is prepared by weighing 175 mg of the compound into a suitable vessel and adding approximately 80% of the required volume of the carrier. Using an aqueous solution of hydrochloric acid, the pH is adjusted to pH2 and the resulting mixture is magnetically stirred until a solution is formed. The formulation is then made up to volume with carrier and the pH is adjusted to pH4 using an aqueous solution of sodium hydroxide.

Example 34 Tablet Composition

Tablets, each weighing 0.15 g and containing 25 mg of a compound of the invention are manufactured as follows:

Composition for 10,000 Tablets

| | |
|---|---|
| Compound of the invention | (250 g) |
| Lactose | (800 g) |
| Corn starch | (415 g) |
| Talc powder | (30 g) |
| Magnesium stearate | (5 g) |

The compound of the invention, lactose and half of the corn starch are mixed. The mixture is then forced through a sieve 0.5 mm mesh size. Corn starch (10 g) is suspended in warm water (90 mL). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 35 Injectable Formulation

| | |
|---|---|
| Compound of the invention | 200 mg |
| Hydrochloric Acid Solution 0.1M or Sodium Hydroxide Solution 0.1M q.s. to pH | 4.0 to 7.0 |
| Sterile water q.s. to | 10 mL |

The compound of the invention is dissolved in most of the water (35° C.-40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

Example 36 Intramuscular Injection

| | |
|---|---|
| Compound of the invention | 200 mg |
| Benzyl Alcohol | 0.10 g |
| Glycofurol 75 | 1.45 g |
| Water for injection q.s to | 3.00 ml |

The compound of the invention is dissolved in the glycofurol. The benzyl alcohol is then added and dissolved, and water added to 3 mL. The mixture is then filtered through a sterile micropore filter and sealed in sterile 3 mL glass vials (type 1).

Example 37 Syrup Formulation

| | |
|---|---|
| Compound of invention | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention is dissolved in a mixture of the glycerol and most of the purified water. An aqueous solution of the sodium benzoate is then added to the solution, followed by addition of the sorbital solution and finally the flavour. The volume is made up with purified water and mixed well.

The invention claimed is:

1. A compound which is a pyrimidine derivative of formula (I):

(I)

wherein:
Z is a direct bond or —(CH$_2$)$_n$— wherein n is 1 or 2;
one of X and Y is N, CH or CF, and the other of X and Y is CH;
one of R$^1$ and R$^2$ is selected from —NHR, —NR$_2$, —OR, —SR, —S(O)R, —S(O)$_2$R and a group of the following formula (A):

(A)

—(NH)$_p$—(CH$_2$)$_q$—V$\begin{array}{c}(R^3)_r\\W\end{array}$ and the other of R$^1$ and R$^2$ is selected from —NHR', —OH, —OR' and a group of the above formula (A);
R is unsubstituted C$_1$-C$_6$alkyl;
R' is a group selected from C$_1$-C$_6$alkyl, 5- to 12-membered aryl and C$_3$-C$_6$ cycloalkyl, which group is unsubstituted or substituted;
W is —(CH$_2$)$_m$—, —CH$_2$—O—CH$_2$—, —CH$_2$—S—CH$_2$— or —CH$_2$—S(O)$_2$—CH$_2$—;
m is an integer of 1 to 4;
p is 1, q is an integer of 1-6 and V is N; or p is 1, q is 0 and V is CH; or p is 0, q is 0 and V is N;
r is 0 or 1; and
R$^3$ is —(CH$_2$)$_s$—NH$_2$ or —(CH$_2$)$_s$—OH wherein s is 0 or an integer of 1 to 4;
or a pharmaceutically acceptable salt thereof.

2. A compound according to claim 1 wherein R' is a group selected from C$_1$-C$_6$ alkyl, 5- to 12-membered aryl and C$_3$-C$_6$ cycloalkyl, which group is unsubstituted or substituted by R, —OH, —OR, —CF$_3$, —S(O)$_2$R, —CN, —NH$_2$, —NHR or NR$_2$, wherein R is as defined in claim 1.

3. A compound according to claim 1 wherein Z is a direct bond.

4. A compound according to claim 1 wherein at least one of R$^1$ and R$^2$ is a group of formula (A).

5. A compound according to claim 1 wherein the group of formula (A) is selected from the following structures:

6. A compound according to claim 1 which is selected from:
  1'-((2-(3-Aminopyrrolidin-1-yl)-4-(isopentylamino)pyrimidin-5-yl)methyl)-6'-fluorospiro[cyclopropane-1,3'-indolin]-2'-one;
  1'-((2-(3-Aminopyrrolidin-1-yl)-4-(((1r,4r)-4-hydroxycyclohexyl)amino)pyrimidin-5-yl)methyl)-6'-fluorospiro[cyclopropane-1,3'-indolin]-2'-one;
  1'-((2-(3-Aminopyrrolidin-1-yl)-4-((2-morpholinoethyl)amino)pyrimidin-5-yl)methyl)-6'-fluorospiro[cyclopropane-1,3'-indolin]-2'-one;
  1'-((2-(3-Aminopyrrolidin-1-yl)-4-((4-hydroxybutyl)amino)pyrimidin-5-yl)methyl)-6'-fluorospiro[cyclopropane-1,3'-indolin]-2'-one;
  1'-((2-(3-Aminopyrrolidin-1-yl)-4-(isobutylamino)pyrimidin-5-yl)methyl)-6'-fluorospiro[cyclopropane-1,3'-indolin]-2'-one;
  1'-((2-(4-Aminomethyl)piperidin-1-yl)-4-(isobutylamino)pyrimidin-5-yl)methyl)-6'-fluorospiro[cyclopropane-1,3'-indolin]-2'-one;
  6'-Fluoro-1'-((4-(isopentylamino)-2-(pyrrolidin-1-yl)pyrimidin-5-yl)methyl)spiro[cyclopropane-1,3'-indolin]-2'-one;
  6'-Fluoro-1'-((4-(isobutylamino)-2-morpholinopyrimidin-5-yl)methyl)spiro[cyclopropane-1,3'-indolin]-2'-one;
  1'-((2-(3-Aminopyrrolidin-1-yl)-4-morpholinopyrimidin-5-yl)methyl)-6'-fluorospiro[cyclopropane-1,3'-indolin]-2'-one;
  1'-((2-(3-Aminopyrrolidin-1-yl)-4-((3-methoxypropyl)amino)pyrimidin-5-yl)methyl)-6'-fluorospiro[cyclopropane-1,3'-indolin]-2'-one;
  1'-((2-(3-Aminopyrrolidin-1-yl)-4-((3-methoxypropyl)amino)pyrimidin-5-yl)methyl)-6'-fluorospiro[cyclopropane-1,3'-indolin]-2'-one;
  1'-((4-(3-Aminopyrrolidin-1-yl)-2-((4-hydroxybutyl)amino)pyrimidin-5-yl)methyl)-6'-fluorospiro[cyclopropane-1,3'-indolin]-2'-one;
  1'-((2-(3-Aminopyrrolidin-1-yl)-4-(1,1-dioxidothiomorpholino)pyrimidin-5-yl)methyl)-6'-fluorospiro[cyclopropane-1,3'-indolin]-2'-one;

1'-{[2-(3-Aminopyrrolidin-1-yl)-4-(4-methanesulfonylpiperazin-1-yl)pyrimidin-5-yl]methyl}-6'-fluoro-1',2' dihydrospiro[cyclopropane-1,3'-indole]-2'-one;

1-[2-(3-Aminopyrrolidin-1-yl)-5-({6'-fluoro-2'-oxo-1',2'-dihydrospiro[cyclopropane-1,3'-indole]-1'-yl}methyl)pyrimidin-4-yl]pyrrolidine-2-carboxamide;

1'-{[2-(3-Aminopyrrolidin-1-yl)-4-[(4-hydroxybutyl)sulfanyl]pyrimidin-5-yl]methyl}-6'-fluoro-1',2'-dihydrospiro[cyclopropane-1,3'-indole]-2'-one;

1'-{[4-(4-Acetylpiperazin-1-yl)-2-(3-aminopyrrolidin-1-yl)pyrimidin-5-yl]methyl}-6'-fluoro-1',2'-dihydrospiro[cyclopropane-1,3'- indole]-2'-one;

1'-{[2-(3-Aminopyrrolidin-1-yl)-4-[(2-methanesulfonylethyl)amino]pyrimidin-5-yl]methyl}-6'-fluoro-1',2'-dihydrospiro[cyclopropane-1,3'-indole]-2'-one;

1'-{[2-(3-Aminopyrrolidin-1-yl)-4-[(5-hydroxypentyl)amino]pyrimidin-5-yl]methyl}-6'-fluoro-1',2'-dihydrospiro[cyclopropane-1,3'-indole]-2'-one;

1'-{[2-(3-Aminopyrrolidin-1-yl)-4-[(4-hydroxycyclohexyl)amino]pyrimidin-5-yl]methyl}-6'-fluoro-1',2'-dihydrospiro[cyclobutane-1,3'-indole]-2'-one;

1'-{[2-(3-Aminopyrrolidin-1-yl)-4-(5-hydroxypent-1-yn-1-yl)pyrimidin-5-yl]methyl}-6'-fluoro-1',2'-dihydrospiro[cyclopropane-1,3'-indole]-2'-one;

1'-{[2-(3-Aminopyrrolidin-1-yl)-4-(3-fluoropropoxy)pyrimidin-5-yl]methyl}-6'-fluoro-1',2'-dihydrospiro[cyclopropane-1,3'-indole]-2'-one;

1'-{[2-(3-Aminopyrrolidin-1-yl)-4-{[(oxan-4-yl)methyl]amino}pyrimidin-5-yl]methyl}-6'-fluoro-1',2'-dihydrospiro[cyclopropane-1,3'-indole]-2'-one;

1'-{[2-(4-Aminopiperidin-1-yl)-4-[(4-hydroxybutyl)amino]pyrimidin-5-yl]methyl}-6'-fluoro-1',2'-dihydrospiro[cyclopropane-1,3'-indole]-2'-one;

1'-({2-[(2-Aminoethyl)amino]-4-[(4-hydroxybutyl)amino]pyrimidin-5-yl}methyl)-6'-fluoro-1',2'-dihydrospiro[cyclopropane-1,3'-indole]-2'-one;

1'-{[2-(3-Aminopyrrolidin-1-yl)-4-[(2-hydroxyethyl)amino]pyrimidin-5-yl]methyl}-6'-fluoro-1',2'-dihydrospiro[cyclopropane-1,3'-indole]-2'-one;

1'-{[2-(3-Aminopyrrolidin-1-yl)-4-[(3-hydroxypropyl)amino]pyrimidin-5-yl]methyl}-6'-fluoro-1',2'-dihydrospiro[cyclopropane-1,3'-indole]-2'-one;

1'-{[2-(3-Aminopyrrolidin-1-yl)-4-(propylamino)pyrimidin-5-yl]methyl}-6'-fluoro-1',2'-dihydrospiro[cyclopropane-1,3'-indole]-2'-one; and 1'-{[2-(3-Aminopyrrolidin-1-yl)-4-(ethylamino)pyrimidin-5-yl]methyl}-6'-fluoro-1',2'-dihydrospiro[cyclopropane-1,3'-indole]-2'-one;

and the pharmaceutically acceptable salts thereof.

7. A pharmaceutical composition which comprises a compound as defined in claim 1 and a pharmaceutically acceptable carrier or diluent.

8. A method of treating a subject suffering from or susceptible to an RSV infection, which method comprises administering to said subject an effective amount of a compound as defined in claim 1.

9. A pharmaceutical composition which comprises (a) a compound as defined in any one of claim 1, and (b) one or more further therapeutic agents together with a pharmaceutically acceptable carrier or diluent, wherein the further therapeutic agent is selected from the group consisting of:
(i) a RSV nucleocapsid(N)-protein inhibitor;
(ii) another protein inhibitor;
(iii) an anti-RSV monoclonal antibody;
(iv) an immunomodulating toll-like receptor compound;
(v) another respiratory virus anti-viral; and
(vi) an anti-inflammatory compound.

10. A process for producing a pharmaceutically acceptable salt as defined in claim 1, which process comprises treating a pyrimidine of formula (I) as defined in claim 1 with a suitable acid in a suitable solvent.

11. A process according to claim 10, wherein the acid is selected from hydrochloric acid, hydrobromic acid, hydroiodic acid, sulphuric acid, nitric acid, phosphoric acid, methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.

12. A method according to claim 8, which method further comprises administering to the subject a further therapeutic agent selected from the group consisting of:
(i) a RSV nucleocapsid(N)-protein inhibitor;
(ii) another protein inhibitor;
(iii) an anti-RSV monoclonal antibody;
(iv) an immunomodulating toll-like receptor compound;
(v) another respiratory virus anti-viral; and
(vi) an anti-inflammatory compound.

13. A pharmaceutical composition according to claim 9, wherein the further therapeutic agent is selected from the group consisting of:
(i) a protein inhibitor that inhibits the phosphoprotein (P) protein and/or large (L) protein;
(ii) an F-protein antibody; and
(iii) an anti-influenza and/or anti-rhinovirus compound.

14. A method according to claim 12, wherein the further therapeutic agent is selected from the group consisting of:
(i) a protein inhibitor that inhibits the phosphoprotein (P) protein and/or large (L) protein;
(ii) an F-protein antibody; and
(iii) an anti-influenza and/or anti-rhinovirus compound.

* * * * *